(12) United States Patent
Wegman

(10) Patent No.: US 8,586,800 B2
(45) Date of Patent: Nov. 19, 2013

(54) GAS PHASE HYDROFORMYLATION PROCESS

(75) Inventor: Richard W. Wegman, South Charleston, WV (US)

(73) Assignee: Dow Technology Investments LLC

( * ) Notice: Subject to any disclaimer, the term of this patent is extended or adjusted under 35 U.S.C. 154(b) by 0 days.

(21) Appl. No.: 13/499,317

(22) PCT Filed: Oct. 6, 2010

(86) PCT No.: PCT/US2010/051576
§ 371 (c)(1),
(2), (4) Date: Mar. 30, 2012

(87) PCT Pub. No.: WO2011/046781
PCT Pub. Date: Apr. 21, 2011

(65) Prior Publication Data
US 2012/0190894 A1 Jul. 26, 2012

Related U.S. Application Data

(60) Provisional application No. 61/252,450, filed on Oct. 16, 2009.

(51) Int. Cl.
*C07C 45/50* (2006.01)

(52) U.S. Cl.
USPC .......................................... 568/454; 568/451

(58) Field of Classification Search
USPC .................................. 568/451, 454
See application file for complete search history.

(56) References Cited

U.S. PATENT DOCUMENTS

| | | |
|---|---|---|
| 3,352,924 A | 11/1967 | Gladrow et al. |
| 3,415,906 A | 12/1968 | Shepard et al. |
| 3,527,809 A | 9/1970 | Pruett et al. |
| 3,847,997 A | 11/1974 | Allen |
| 4,045,493 A | 8/1977 | Trevillyan |
| 4,098,727 A | 7/1978 | Haag et al. |
| 4,144,191 A | 3/1979 | Hartwell et al. |
| 4,148,830 A | 4/1979 | Pruett et al. |
| 4,185,038 A | 1/1980 | Carlock |
| 4,361,711 A | 11/1982 | Blaskie et al. |
| 4,386,013 A | 5/1983 | Callahan et al. |
| 4,487,972 A | 12/1984 | Haag et al. |
| 4,504,684 A | 3/1985 | Fox et al. |
| 4,567,302 A | 1/1986 | Sivaramakrishnan |
| 4,567,306 A | 1/1986 | Dennis et al. |
| 4,599,206 A | 7/1986 | Billig et al. |
| 4,668,651 A | 5/1987 | Billig et al. |
| 4,717,775 A | 1/1988 | Billig et al. |
| 4,748,261 A | 5/1988 | Billig et al. |
| 4,769,498 A | 9/1988 | Billig et al. |
| 4,774,361 A | 9/1988 | Maher et al. |
| 4,835,299 A | 5/1989 | Maher et al. |
| 4,885,401 A | 12/1989 | Billig et al. |
| 5,093,297 A | 3/1992 | Woo et al. |
| 5,113,022 A | 5/1992 | Abatjoglou et al. |
| 5,179,055 A | 1/1993 | Wink et al. |
| 5,183,943 A | 2/1993 | Bryant et al. |
| 5,202,297 A | 4/1993 | Lorz et al. |
| 5,235,113 A | 8/1993 | Sato et al. |
| 5,254,741 A | 10/1993 | Lorz et al. |
| 5,264,616 A | 11/1993 | Roeper et al. |
| 5,277,532 A | 1/1994 | Pazzaglia |
| 5,312,996 A | 5/1994 | Packett |
| 5,364,950 A | 11/1994 | Babin et al. |
| 5,391,801 A | 2/1995 | Sato et al. |
| 5,409,877 A | 4/1995 | Takeuchi et al. |
| 5,741,942 A | 4/1998 | Bryant et al. |
| 5,789,333 A | 8/1998 | Angelici et al. |
| 5,874,640 A | 2/1999 | Bryant et al. |
| 5,892,119 A | 4/1999 | Bryant et al. |
| 6,090,987 A | 7/2000 | Billig et al. |
| 6,121,184 A | 9/2000 | Druliner et al. |
| 6,229,052 B1 | 5/2001 | Bunel et al. |
| 6,294,700 B1 | 9/2001 | Kanel et al. |
| 6,307,110 B1 | 10/2001 | Argyropoulos et al. |
| 6,362,354 B1 | 3/2002 | Bunel et al. |
| 6,369,257 B1 | 4/2002 | Bunel et al. |
| 6,380,421 B1 | 4/2002 | Lu et al. |
| 6,437,192 B1 | 8/2002 | Bunel |
| 6,544,923 B1 | 4/2003 | Huang et al. |

OTHER PUBLICATIONS

Lindner, et al., "Chemistry in Interphases—A New Approach to Organometallic Syntheses and Catalysis", Angew. Chem. Int. Ed. 1999, 38, 2154-2174.
Yermakov, et al., "Catalysis by Supported Complexes", Studies in Surf. Sci. and Cat., 8, 1981, pp. 1-58.
OECD Guidelines for the Testing of Chemicals, vol. 105, "Water Solubility", Jul. 27, 1995, pp. 1-7.
Riisager, et al., "Propene Hydroformylation by Supported Aqueous-Phase Rh-NORBOS Catalysts", Journal of Molecular Catalysis A: Chemical 193 (2003) 259-272.

*Primary Examiner* — Sikarl Witherspoon
(74) *Attorney, Agent, or Firm* — Paul D. Hayhurst

(57) ABSTRACT

A gas phase catalytic hydroformylation process for producing at least one aldehyde product in the presence of a transition metal-ligand complex hydroformylation catalyst and water vapor. Surprisingly, catalyst activity can be sustained by having traces of water vapor in the feed stream. Additionally, additional ligand can be added to replace lost ligand to maintain activity. In addition, it has been found that treatment of the catalyst with a buffer can rejuvenate catalyst activity.

12 Claims, 5 Drawing Sheets

GAS PHASE HYDROFORMYLATION PROCESS

CROSS-REFERENCE TO RELATED APPLICATIONS

This application claims priority from U.S. provisional application Ser. No. 61/252,450, filed Oct. 16, 2009, which is incorporated herein by reference in its entirety.

BACKGROUND OF THE INVENTION

This disclosure pertains to an improved process for hydroformylating an olefinically-unsaturated compound to produce one or more aldehyde products.

It is well known in the art that aldehydes may be readily produced by reacting an olefinically unsaturated compound in the liquid phase with gaseous carbon monoxide and hydrogen in the presence of a metal-organophosphorus ligand complex catalyst, and that preferred processes involve continuous hydroformylation and recycling of a solution containing a Group VIII-organopolyphosphite ligand complex catalyst. Rhodium is a preferred Group VIII metal. Such art is exemplified in U.S. Pat. No. 4,148,830; U.S. Pat. No. 4,717,775; and U.S. Pat. No. 4,769,498. For the purposes of this document, such processes are hereinafter referred to as "liquid phase" processes. Aldehydes produced by such processes have a wide range of utility, for example, as intermediates for hydrogenation to aliphatic alcohols, for amination to aliphatic amines, for oxidation to aliphatic acids, and for aldol condensation to produce plasticizers. The process normally produces a mixture of branched and unbranched isomeric products.

The art recognizes that normal or unbranched aldehydes generally provide more value than their iso- or branched isomers. Additionally, it is known that the ratio of normal to branched isomers is a function of carbon monoxide partial pressure, and typically lower carbon monoxide partial pressures give products with higher normal to branched ratios. Rhodium-organopolyphosphite ligand complex catalyzed liquid phase processes have been shown to give very desirable normal to branched isomer ratios.

Heterogeneous versions of homogeneous catalyst systems are very common. Generally, a heterogeneous analog is less active and selective but offers the advantages of easier catalyst/product separation and better heat removal. Much work over the years has been carried out to develop a viable heterogeneous hydroformylation catalyst. The early catalysts were supported metal oxides, such as rhodium, on silica as reported in U.S. Pat. No. 3,352,924, U.S. Pat. No. 4,185,038, U.S. Pat. No. 4,361,711, U.S. Pat. No. 4,386,013, U.S. Pat. No. 4,456,694, and U.S. Pat. No. 5,409,877. These catalysts were typically non-selective in terms of normal to iso (n/i) aldehydes and generated high levels of hydrocarbons due to hydrogenation Immobilized hydroformylation catalysts are reported in U.S. Pat. No. 3,847,997, U.S. Pat. No. 4,487,972, U.S. Pat. No. 4,098,727, U.S. Pat. No. 4,045,493, U.S. Pat. No. 4,504,684, U.S. Pat. No. 5,093,297, and U.S. Pat. No. 4,144,191. In these cases, the hydroformylation catalysts are bonded to the support, such as a resin, through some type of anionic or acid/base bonding. Generally, this type of catalyst is used in a liquid phase reaction as a slurry. Although good activity and selectivity can be obtained, the catalysts leach the metal into the reaction liquid over time, rendering any catalyst/product separation advantage moot. An alternative approach is to tether a ligand to a support/resin. The tethered ligand/resin is then reacted with a metal complex to form a bound metal-ligand catalyst precursor as reported in U.S. Pat. No. 5,789,333, U.S. Pat. No. 6,544,923, U.S. Pat. No. 6,121,184, U.S. Pat. No. 6,229,052, U.S. Pat. No. 6,362,354, U.S. Pat. No. 6,369,257, U.S. Pat. No. 6,380,421, and U.S. Pat. No. 6,437,192. Leaching of the metal is also a problem with tethered catalysts. U.S. Pat. No. 6,229,052 and U.S. Pat. No. 6,369,257 disclose using rhodium/grafted polymers as fixed bed vapor phase catalysts for hydroformylating propylene. The vapor phase catalyst gave results similar to the slurried version, albeit with lower conversion and activity. Significant activity decline was also observed with the vapor phase catalyst.

Accordingly, it would be desirable to have a gas phase hydroformylation process that would be able to maintain substantially stable activity over time compared to the processes of the prior art.

SUMMARY OF THE INVENTION

The disclosure includes a hydroformylation process for production of at least one aldehyde product, the process comprising contacting under gas phase reaction conditions carbon monoxide, hydrogen and one or more olefinically-unsaturated compounds in the presence of a hydroformylation catalyst, wherein the catalyst comprises a catalytic metal and a ligand comprising at least one organophosphite ligand, wherein the catalyst is physisorbed on a support, and wherein water vapor is present at least part of the time.

Surprisingly, it has been found that the normal to branched ratio of the product aldehyde is similar to that found for the liquid phase catalysts. In particular, it has been discovered that a gas phase catalyst having a metal-organophosphite-support leads to very high ratio of normal to branched isomers of aldehyde products. The advantage of the metal-organophosphite-support catalyst is that it does not have to be separated from the product.

It has been further surprisingly found that catalyst activity can be sustained by having traces of water vapor in the feed stream. Additionally, additional ligand can be added to replace lost ligand to maintain activity. In addition, it has been found that treatment of the catalyst with a buffer can rejuvenate catalyst activity.

DETAILED DESCRIPTION OF THE INVENTION

Figure 1:
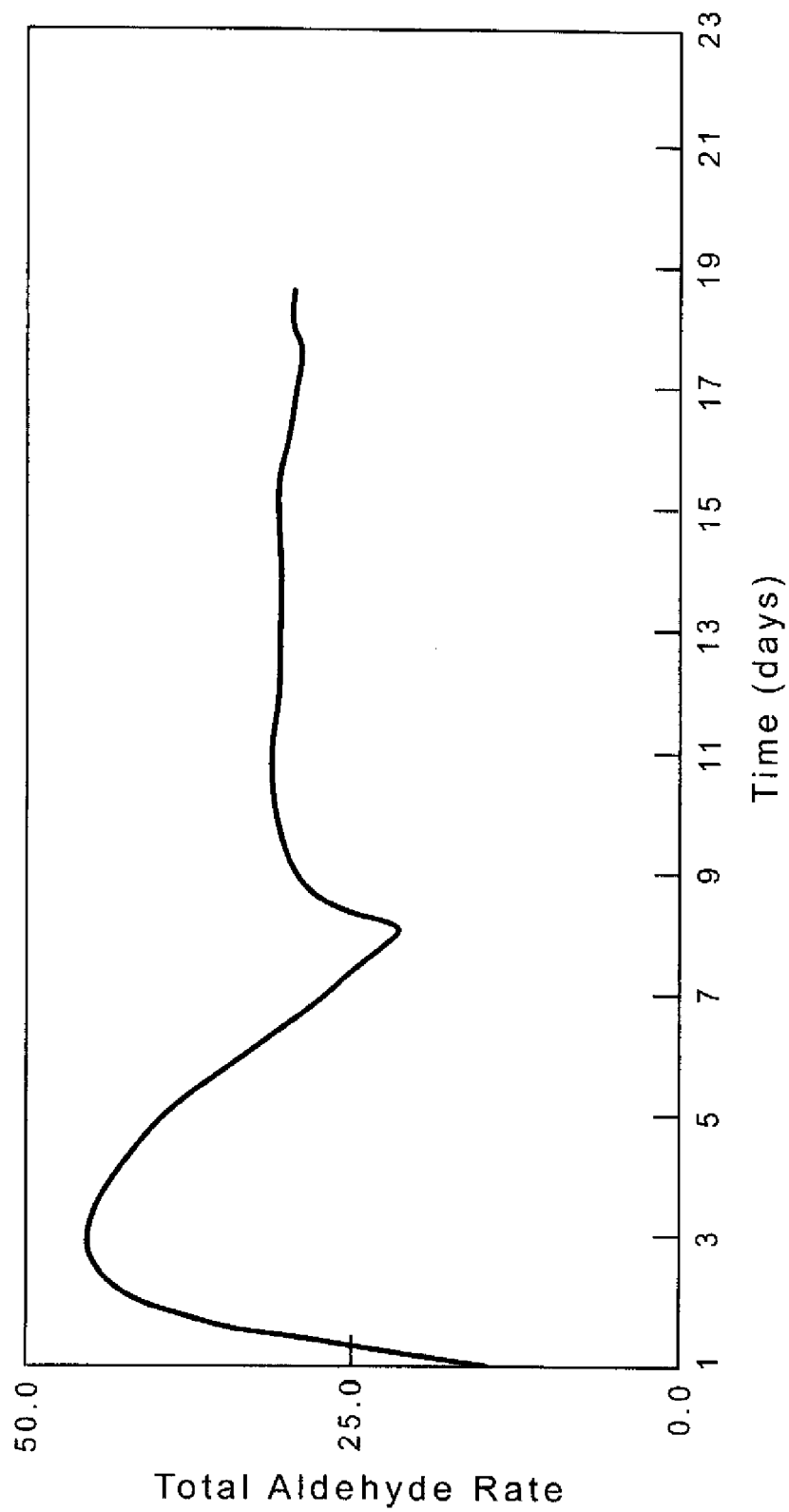
FIG. 1 is a plot of the rate of product formation expressed in $lb/ft^3$ cat-hr. as a function of on-stream time for Example 3.

The gas phase hydroformylation process of this disclosure employs an olefinically-unsaturated compound, carbon monoxide, hydrogen, and a transition metal-ligand complex hydroformylation catalyst to hydroformylate the olefin to the corresponding aldehyde(s) in the gas phase, in the presence of water vapor during at least part of the process. Optionally, the process includes adding additional ligand to the process, and optionally includes contacting the catalyst with a buffer.

The catalyst of the disclosure is a discrete metal-ligand complex residing on a support. The term "physisorbed" is well-known to those skilled in the art, and the term "physisorbed on the support," in the context of the metal-ligand complex, means that there is substantially no sigma bonding between any atom of the complex and any atom of the support. Thus, the metal-ligand complex is physisorbed on the support. The combination of metal-ligand complex and support is referred to herein as the catalyst or supported catalyst.

The term "gas phase" as used herein means the vapor or gaseous phase. For example, the reaction gas is in the gas phase when it is above its dew point.

As used herein, "a," "an," "the," "at least one," and "one or more" are used interchangeably. The terms "comprises," "includes," and variations thereof do not have a limiting meaning where these terms appear in the description and claims. Thus, for example, an aqueous composition that includes particles of "a" hydrophobic polymer can be interpreted to mean that the composition includes particles of "one or more" hydrophobic polymers.

Also herein, the recitations of numerical ranges by endpoints include all numbers subsumed in that range (e.g., 1 to 5 includes 1, 1.5, 2, 2.75, 3, 3.80, 4, 5, etc.).

Also herein, the recitations of numerical ranges and/or numerical values, including such recitations in the claims, can be read to include the term "about." In such instances the term "about" refers to numerical ranges and/or numerical values that are substantially the same as those recited herein.

The substituted or unsubstituted olefinic compound employable in the hydroformylation process of this disclosure can include both optically active (prochiral and chiral) and non-optically active (achiral) unsaturated compounds containing from 2 to 8, preferably 3 to 6, carbon atoms and one or more carbon-carbon double bonds (C=C). Such olefinic compound can be terminally or internally unsaturated and be of straight-chain, branched chain, or cyclic structures. Moreover, such olefin compounds may further contain one or more ethylenically unsaturated groups. Olefin mixtures can be employed, such as mixed butenes; for example, raffinate I and raffinate II are known to the skilled person. Such olefinic compounds and the corresponding aldehyde products derived therefrom may also contain one or more groups or substituents that do not adversely affect the hydroformylation process of this disclosure; suitable groups or substituents being described, for example, in U.S. Pat. No. 3,527,809, and U.S. Pat. No. 4,769,498, incorporated herein by reference.

In one embodiment, the process of the subject disclosure is especially useful for the production of non-optically active aldehydes, by hydroformylating achiral alpha-olefins containing from 2 to 8, preferably 3 to 6, carbon atoms, and achiral internal olefins containing from 4 to 8 carbon atoms as well as starting material mixtures of such alpha olefins and internal olefins.

Illustrative alpha and internal olefins include, for example, ethylene, propylene, 1-butene, 1-pentene, 1-hexene, 1-heptene, 1-octene, 2-butene, 2-methyl propene(isobutylene), 2-methylbutene, 2-pentene, 2-hexene, 3-hexene, 2-heptene, 2-octene, cyclohexene, propylene dimers, butadiene, piperylene, isoprene, 2-ethyl-1-hexene, styrene, 3-phenyl-1-propene, 1,4-hexadiene, 1,7-octadiene, and the like, as well as, 1,3-dienes, butadiene, alkyl alkenoates, for example, methyl pentenoate; alkenyl alkanoates, alkenyl alkyl ethers, alkenols, for example, pentenols; alkenals, for example, pentenals; such species to include allyl alcohol, allyl butyrate, hex-1-en-4-ol, oct-1-en-4-ol, vinyl acetate, allyl acetate, 3-butenyl acetate, vinyl propionate, allyl propionate, methyl methacrylate, vinyl ethyl ether, vinyl methyl ether, allyl ethyl ether, 3-butenenitrile, 5-hexenamide, eugenol, iso-eugenol, safrole, iso-safrole, anethol, 4-allylanisole, indene, limonene, beta-pinene. Illustrative of suitable substituted and unsubstituted olefinic starting materials include those olefinic compounds described in Kirk-Othmer, *Encyclopedia of Chemical Technology, Fourth Edition,* 1996, the pertinent portions of which are incorporated herein by reference.

Hydrogen and carbon monoxide are also required for the process of this disclosure. These gases may be obtained from any available source, including petroleum cracking and refinery operations. Synthesis gas mixtures are preferably employed. Any hydrocarbon-containing feed stream that can be converted into a feedstock comprising carbon monoxide and hydrogen, most preferably a synthesis gas (or "syn gas"), is useful in the processes of this disclosure. The ratio of hydrogen to carbon monoxide in the reaction zone is from about 1:10 to about 100:1 or higher, from about 50:1 to about 1:50, preferably about 20:1 to about 1:20, more preferably from about 10:1 to about 1:10. Useful feed streams include natural gas (mainly methane, but natural gas composition can vary depending on location and source), naphtha, refinery off-gas, LPG, gas oil, vacuum residuals, shale oils, asphalts, various types of fuel oils, and hydrocarbon containing process recycle streams. In one embodiment, methanol can be converted into feed components comprising carbon monoxide and hydrogen, e.g., synthesis gas. Further, hydrogen may be formed in situ, for example, by the water-gas shift reaction.

Feedstocks comprising carbon monoxide and hydrogen, e.g., synthesis gas, may undergo purification prior to being fed to any reaction zones. For use in the process of this disclosure, the synthesis gas preferably is essentially free of catalyst poisons and inhibitors such as hydrogen sulfide, carbonyl sulfide, metal carbonyls, e.g., iron carbonyl and nickel carbonyl, ammonia, basic organic compounds, e.g., methyl amine and ethyl amine, and generally any compounds that will neutralize an acid.

The catalyst comprises a discrete metal-ligand complex physisorbed on a support. Preferably, the hydroformylation catalyst comprises a metal-organophosphite ligand complex catalyst, wherein the ligand comprises, for example, an organomonophosphite ligand, an organopolyphosphite ligand, or a combination thereof. More preferably, the hydroformylation catalyst comprises a metal-organopolyphosphite ligand complex catalyst.

The catalyst of this invention may be preformed by adding a metal-ligand complex to a support or may be formed in situ by adding metal precursors and ligands to the support.

Suitable metals of the transition metal-ligand complex catalyst include, for example, Group VIII metals selected from rhodium (Rh), cobalt (Co), iridium (Ir), ruthenium (Ru), iron (Fe), nickel (Ni), palladium (Pd), platinum (Pt), osmium (Os) and mixtures thereof, with the preferred metals being rhodium, cobalt, iridium and ruthenium, more preferably rhodium, cobalt and ruthenium, and most preferably, rhodium. Other permissible metals include Group VIA metals selected from chromium (Cr), molybdenum (Mo), tungsten (W), and mixtures thereof. Mixtures of metals, such as mixtures from Groups VIA and VIII, may also be used. Groups VIA and VIII metals are defined in "Chemistry of the Elements," Greenwood and Earnshaw, Pergamon Press, 1984.

In addition to the transition metal-organophosphite ligand complex catalyst, free organophosphite ligand may also be present in the reaction zone. In this disclosure, the generic term "organophosphite ligand" embraces both organopolyphosphite and organomonophosphite types of ligands. The organophosphite ligands may be complexed or unbound as catalytic cycling and competition between ligands for transition metal may dictate. By "free organophosphite ligand" is meant an organophosphite ligand that is not complexed with (tied to or bound to) the metal, such as a rhodium atom, of the complex catalyst.

The organophosphite ligand preferably comprises an organopolyphosphite ligand. It is believed that when carbon monoxide and hydrogen are present the metal is directly bonded with the ligand, carbon monoxide and hydrogen. For the purposes of this disclosure, the term "ligand" will refer to the organophosphorous species unless otherwise noted, although it is recognized that CO and hydrogen are also ligands.

The term "complex" as used herein means a coordination compound formed by the union of one or more electronically rich molecules or atoms (i.e., ligand) with one or more electronically poor molecules or atoms (i.e., transition metal). For example, the organomonophosphite ligand employable herein possesses one phosphorus (III) donor atom having one unshared pair of electrons, which is capable of forming a coordinate covalent bond with the metal. The organopolyphosphite ligand employable herein possesses two or more phosphorus (III) donor atoms, each having one unshared pair of electrons, each of which is capable of forming a coordinate covalent bond independently or possibly in concert (for example, via chelation) with the transition metal. Carbon monoxide can also be present and complexed with the metal. The ultimate composition of the complex catalyst may also contain an additional non-phosphite ligand, e.g., hydrogen or an anion satisfying the coordination sites or nuclear charge of the metal. Illustrative additional non-phosphite ligands include, for example, halogen (Cl, Br, I), alkyl, aryl, substituted aryl, acyl, $CF_3$, $C_2F_5$, CN, $(R)_2PO$ and $RP(O)(OH)O$ (wherein each R is the same or different and is a substituted or unsubstituted hydrocarbon radical, e.g., alkyl or aryl), acetate, acetylacetonate, $SO_4$, $PF_4$, $PF_6$, $NO_2$, $NO_3$, $CH_3O$, $CH_2=CHCH_2$, $CH_3CH=CHCH_2$, $C_2H_5CN$, $CH_3CN$, $NH_3$, pyridine, $(C_2H_5)_3N$, mono-olefins, diolefins and triolefins, tetrahydrofuran, and the like.

The number of available coordination sites on catalytic metals is well known in the art. Thus, the catalytic species may comprise a complex catalyst mixture, in their monomeric, dimeric or higher nuclearity forms, which are preferably characterized by at least one organophosphite-containing molecule complexed per one molecule of metal, e.g., rhodium. For instance, it is considered that the catalytic species of the preferred catalyst employed in the hydroformylation reaction may be complexed with carbon monoxide and hydrogen in addition to the organophosphite ligand(s) in view of the carbon monoxide and hydrogen gas employed by the hydroformylation reaction.

The organophosphite ligands comprise at least one phosphite group, each of which contains one trivalent phosphorus atom bonded to three hydrocarbyloxy radicals. Hydrocarbyloxy radicals that link and bridge two phosphite groups are more properly referred to as "divalent hydrocarbyldioxy radicals." These bridging diradicals are not limited to any particular hydrocarbyl species.

The term "aryloxy" as used herein broadly refers to a monovalent substituted or unsubstituted aryl radical bonded to a single ether linkage, as in —O-aryl, wherein the aryl group comprises an aromatic ring or rings. Preferred aryloxy groups contain one aromatic ring, or from 2 to 4 fused or linked aromatic rings, each ring having from about 5 to about 20 carbon atoms such as, for example, phenoxy, naphthyloxy, or biphenoxy. Any of the aforementioned radicals and groups may be unsubstituted or substituted as noted hereinafter.

The term "end group" as used herein broadly refers to a moiety that is pendant from a phosphorus atom and not bridging two phosphite groups (i.e., terminal, non-bridging). In Formula I, below, the end groups are represented by $R^1$ and $R^2$.

The term "end group pair" as used herein broadly refers to two moieties that are pendant from the same phosphorous atom. The term "close ended" as used herein broadly refers to organophosphite ligands wherein the moieties comprising at least two of the end group pairs are bonded to one another (a>=2, b=0). The term "open-ended" as used herein broadly refers to organophosphite ligands wherein the moieties comprising at least one of the end group pairs are not bonded to one another (b>=1). The term "doubly open-ended" as used herein broadly refers to organophosphite ligands wherein the moieties comprising at least two of the end group pairs are not bonded to one another (b>=2).

The preferred organopolyphosphites that may serve as the ligand of the metal-organopolyphosphite ligand complex catalyst and/or free ligand of the hydroformylation processes of this invention may be achiral (optically inactive) or chiral (optically active) and are well known in the art. Achiral organopolyphosphites are preferred. Representative organopolyphosphites contain two or more tertiary (trivalent) phosphorus atoms and may include those having the formula:

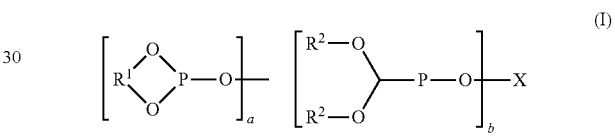

wherein X represents a substituted or unsubstituted n-valent organic bridging radical containing from 2 to 40 carbon atoms, each $R^1$ is the same or different and represents a divalent organic radical containing from 4 to 40 carbon atoms, each $R^2$ is the same or different and represents a substituted or unsubstituted monovalent hydrocarbon radical containing from 1 to 24 carbon atoms, a and b can be the same or different and each have a value of 0 to 6, with the proviso that the sum of a+b is 2 to 6 and n equals a+b. Of course it is to be understood that when a has a value of 2 or more, each $R^1$ radical may be the same or different, and when b has a value of 1 or more, each $R^2$ radical may be the same or different.

Representative n-valent (preferably divalent) hydrocarbon bridging radicals represented by X and representative divalent organic radicals represented by $R^1$ above, include both acyclic radicals and aromatic radicals, such as alkylene, alkylene-Qm-alkylene, cycloalkylene, arylene, bisarylene, arylene-alkylene, and arylene-$(CH_2)_y$-$Q_m$-$(CH_2)_y$-arylene radicals, and the like, wherein each y is the same or different and has a value of 0 or 1, and wherein Q represents a divalent bridging group selected from —$C(R^3)_2$—, —O—, —S—, —$NR^4$—, —$Si(R^5)_2$— and —CO—, wherein each $R^3$ is the same or different and represents hydrogen, an alkyl radical having from 1 to 12 carbon atoms, phenyl, tolyl, and anisyl, $R^4$ represents hydrogen or a substituted or unsubstituted monovalent hydrocarbon radical, e.g., an alkyl radical having 1 to 4 carbon atoms; each $R^5$ is the same or different and represents hydrogen or an alkyl radical, and m has a value of 0 or 1. The more preferred acyclic radicals represented by X and $R^1$ above are divalent alkylene radicals, while the more preferred aromatic radicals represented by X and $R^1$ above are divalent arylene and bisarylene radicals, such as disclosed more fully, for example, in U.S. Pat. Nos. 4,769,498; 4,774, 361; 4,885,401; 5,179,055; 5,113,022; 5,202,297; 5,235,113; 5,264,616; 5,364,950; 5,874,640; 5,892,119; 6,090,987; and 6,294,700 and the like, the disclosures of which are incorporated herein by reference. Representative preferred monovalent hydrocarbon radicals represented by each $R^2$ radical above include alkyl and aromatic radicals. Illustrative preferred organopolyphosphites may include bisphosphites such as those of Formulas (II) to (IV) below:

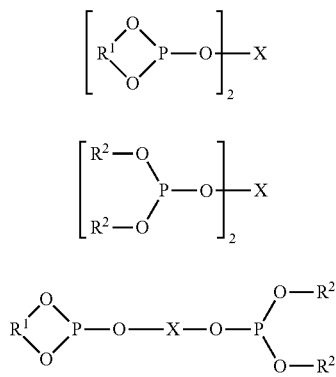

wherein each $R^1$, $R^2$ and X of Formulas (II) to (IV) is the same as defined above for Formula (I). Preferably each $R^1$ and X represent a divalent hydrocarbon radical selected from alkylene, arylene, arylene-alkylene-arylene, and bisarylene, while each $R^2$ radical represents a monovalent hydrocarbon radical selected from alkyl and aryl radicals. Organopolyphosphite ligands of such Formulas (II) to (IV) may be found disclosed, for example, in U.S. Pat. Nos. 4,668,651; 4,748,261; 4,769,498; 4,774,361; 4,885,401; 5,113,022; 5,179,055; 5,202,297; 5,235,113; 5,254,741; 5,264,616; 5,312,996; 5,364,950; and 5,391,801; the disclosures of all of which are incorporated herein by reference.

Representative of more preferred classes of organobisphosphites are those of the following Formulas (V) to (VII):

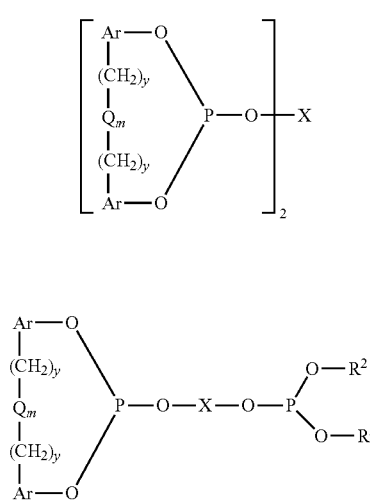

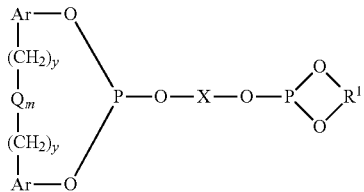

wherein Q, $R^1$, $R^2$, X, m, and y are as defined above, and each Ar is the same or different and represents a substituted or unsubstituted aryl radical. Most preferably X represents a divalent aryl-$(CH_2)_y$-$(Q)_m$-$(CH_2)_y$-aryl radical wherein each y individually has a value of 0 or 1; m has a value of 0 or 1 and Q is —O—, —S— or —$C(R^3)_2$ where each $R^3$ is the same or different and represents hydrogen or a methyl radical. More preferably each alkyl radical of the above defined $R^2$ groups may contain from 1 to 24 carbon atoms and each aryl radical of the above-defined Ar, X, $R^1$ and $R^2$ groups of the above Formulas (V) to (VII) may contain from 6 to 18 carbon atoms and said radicals may be the same or different, while the preferred alkylene radicals of X may contain from 2 to 18 carbon atoms and the preferred alkylene radicals of $R^1$ may contain from 5 to 18 carbon atoms. In addition, preferably the divalent Ar radicals and divalent aryl radicals of X of the above formulas are phenylene radicals in which the bridging group represented by —$(CH_2)_y$-$(Q)_m$-$(CH_2)_y$— is bonded to said phenylene radicals in positions that are ortho to the oxygen atoms of the formulas that connect the phenylene radicals to their phosphorus atom of the formulae. It is also preferred that any substituent radical when present on such phenylene radicals be bonded in the para and/or ortho position of the phenylene radicals in relation to the oxygen atom that bonds the given substituted phenylene radical to its phosphorus atom.

Advantageously, the ligand is not ionic. While not wishing to be bound by any theory, it is thought that ionic ligands will detract from the beneficial aspects of the buffer treatment.

Of course any of the $R^1$, $R^2$, X, Q and Ar radicals of such non-ionic and ionic organopolyphosphites of Formulas (I) to (VII) above may be substituted if desired, with any suitable substituent containing from 1 to 30 carbon atoms that does not adversely affect the desired result of the process of this invention. Substituents that may be on said radicals, in addition of course to corresponding hydrocarbon radicals such as alkyl, aryl, aralkyl, alkaryl and cyclohexyl substituents, include for example silyl radicals such as —$Si(R^7)_3$; amino radicals such as —$N(R^7)_2$; phosphine radicals such as -aryl-$P(R^7)_2$; acyl radicals such as —$C(O)R^7$ acyloxy radicals such as —$OC(O)R^7$; amido radicals such as —$CON(R^7)_2$ and —$N(R^7)COR^7$; sulfonyl radicals such as —$SO_2R^7$, alkoxy radicals such as —$OR^7$; sulfinyl radicals such as —$SOR^7$, sulfenyl radicals such as —$SR^7$, phosphonyl radicals such as —$P(O)(R^7)_2$, as well as halogen, nitro, cyano, trifluoromethyl, hydroxy radicals, and the like, wherein each $R^7$ radical individually represents the same or different monovalent hydrocarbon radical having from 1 to 18 carbon atoms (e.g., alkyl, aryl, aralkyl, alkaryl and cyclohexyl radicals), with the proviso that in amino substituents such as —$N(R^7)_2$ each $R^7$ taken together can also represent a divalent bridging group that forms a heterocyclic radical with the nitrogen atom, and in amido substituents such as —C(O)N(R$^7$)$_2$ and —N(R$^7$)COR$^7$ each R$^7$ bonded to N can also be hydrogen. Of course it is to be understood that any of the substituted or unsubstituted hydrocarbon radicals groups that make up a particular given organopolyphosphite may be the same or different.

More specifically illustrative substituents include primary, secondary and tertiary alkyl radicals such as methyl, ethyl, n-propyl, isopropyl, butyl, sec-butyl, t-butyl, neo-pentyl, n-hexyl, amyl, sec-amyl, t-amyl, iso-octyl, decyl, octadecyl, and the like; aryl radicals such as phenyl, naphthyl and the like; aralkyl radicals such as benzyl, phenylethyl, triphenylmethyl, and the like; alkaryl radicals such as tolyl, xylyl, and the like; alicyclic radicals such as cyclopentyl, cyclohexyl, 1-methylcyclohexyl, cyclooctyl, cyclohexylethyl, and the like; alkoxy radicals such as methoxy, ethoxy, propoxy, t-butoxy, —OCH$_2$CH$_2$OCH$_3$, —O(CH$_2$CH$_2$)$_2$OCH$_3$, —O(CH$_2$CH$_2$)$_3$OCH$_3$, and the like; aryloxy radicals such as phenoxy and the like; as well as silyl radicals such as —Si(CH$_3$)$_3$, —Si(OCH$_3$)$_3$, —Si(C$_3$H$_7$)$_3$, and the like; amino radicals such as —NH$_2$, —N(CH$_3$)$_2$, —NHCH$_3$, —NH(C$_2$H$_5$), and the like; arylphosphine radicals such as —P(C$_6$H$_5$)$_2$, and the like; acyl radicals such as —C(O)CH$_3$, —C(O)C$_2$H$_5$, —C(O)C$_6$H$_5$, and the like; carbonyloxy radicals such as —C(O)OCH$_3$ and the like; oxycarbonyl radicals such as —O(CO)C$_6$H$_5$, and the like; amido radicals such as —CONH$_2$, —CON(CH$_3$)$_2$, —NHC(O)CH$_3$, and the like; sulfonyl radicals such as —S(O)$_2$C$_2$H$_5$ and the like; sulfinyl radicals such as —S(O)CH$_3$ and the like; sulfenyl radicals such as —SCH$_3$, —SC$_2$H$_5$, —SC$_6$H$_5$, and the like; phosphonyl radicals such as —P(O)(C$_6$H$_5$)$_2$, —P(O)(CH$_3$)$_2$, —P(O)(C$_2$H$_5$)$_2$, —P(O)(C$_3$H$_7$)$_2$, —P(O)(C$_4$H$_9$)$_2$, —P(O)(C$_6$H$_{13}$)$_2$, —P(O)CH$_3$(C$_6$H$_5$), —P(O)(H)(C$_6$H$_5$), and the like.

Specific illustrative examples of closed ended organobisphosphite ligands include the following:

6,6'-[[4,4'-bis(1,1-dimethylethyl)-[1,1'-binaphthyl]-2,2'-diyl]bis(oxy)]bis-dibenzo[d,f][1,3,2]-dioxaphosphepin having the formula:

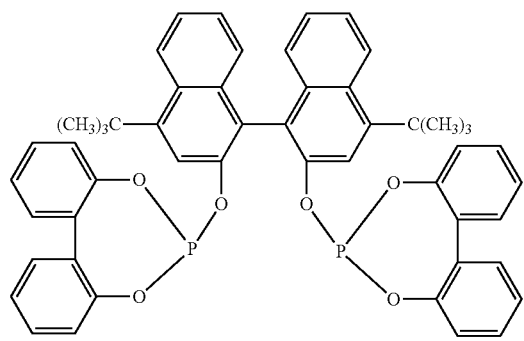

Ligand A 6,6'-[[3,3'-bis(1,1-dimethylethyl)-5,5'-dimethoxy-[1,1'-biphenyl]-2,2'-diyl]bis(oxy)]bis-dibenzo[d,f][1,3,2]dioxaphosphepin having the formula:

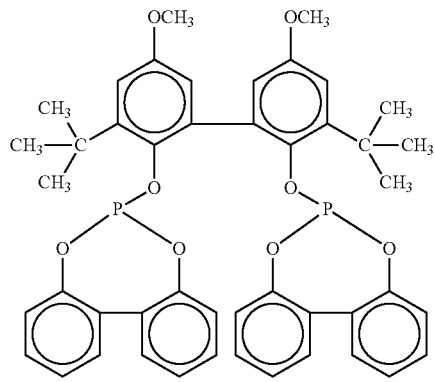

Ligand B 6,6'-[[3,3',5,5'-tetrakis(1,1-dimethylpropyl)-[1,1'-biphenyl]-2,2'-diyl]bis(oxy)]bis-dibenzo[d,f][1,3,2]dioxaphosphepin having the formula:

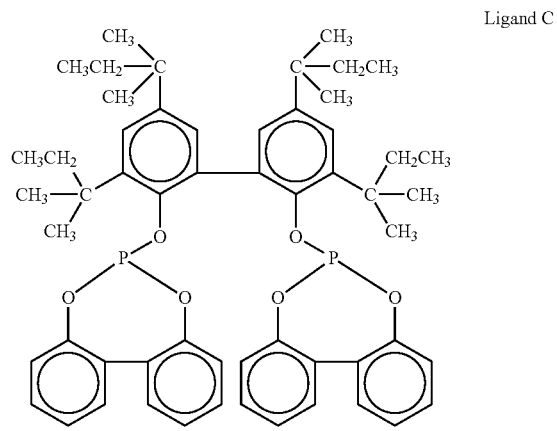

Ligand C 6,6'-[[3,3',5,5'-tetrakis(1,1-dimethylethyl)-[1,1'-biphenyl]-2,2'-diyl]bis(oxy)]bis-dibenzo[d,f][1,3,2]-dioxaphosphepin having the formula:

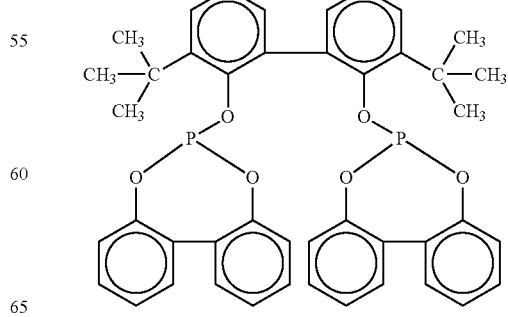

Ligand D (2R,4R)-di[2,2'-(3,3',5,5'-tetrakis-tert-amyl-1,1'-biphenyl)]-2,4-pentyldiphosphite having the formula:

Ligand E

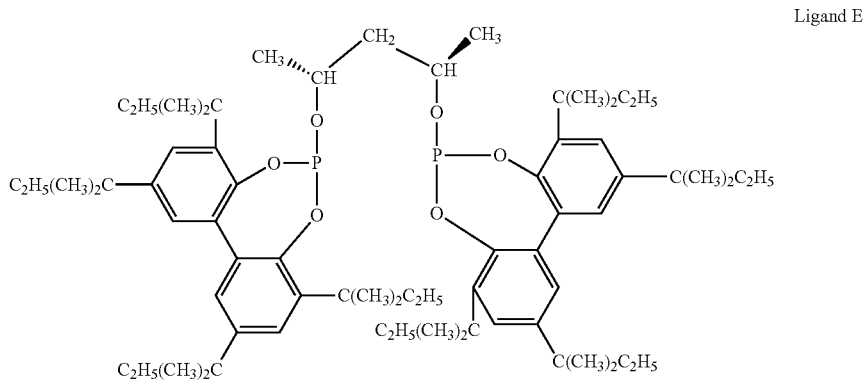

(2R,4R)-di[2,2'-(3,3',5,5'-tetrakis-tert-butyl-1,1'-biphenyl)]-2,4-pentyldiphosphite having the formula:

Ligand F

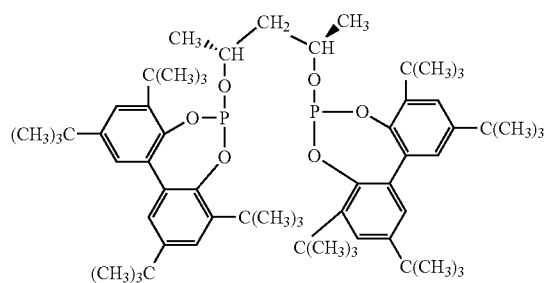

(2R,4R)-di[2,2'-(3,3'-di-amyl-5,5'-dimethoxy-1,1'-biphenyl)]-2,4-pentyldiphosphite having the formula:

Ligand G

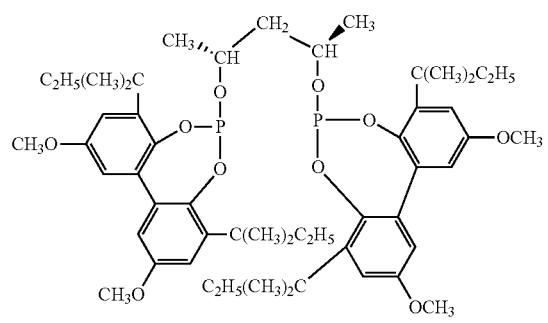

(2R,4R)-di[2,2'-(3,3'-di-tert-butyl-5,5'-dimethyl-1,1'-biphenyl)]-2,4-pentyldiphosphite having the formula:

Ligand H

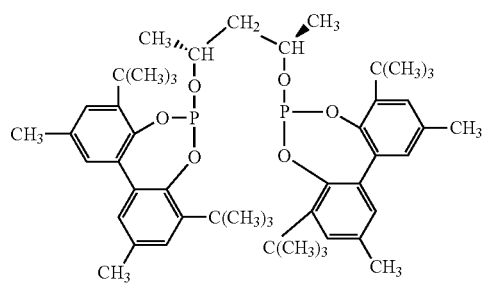

(2R,4R)-di[2,2'-(3,3'-di-tert-butyl-5,5'-diethoxy-1,1'-biphenyl)]-2,4-pentyldiphosphite having the formula:

Ligand I

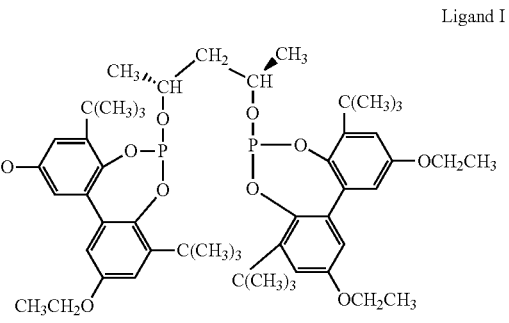

(2R,4R)-di[2,2'-(3,3'-di-tert-butyl-5,5'-diethyl-1,1'-biphenyl)]-2,4-pentyldiphosphite having the formula:

Ligand J

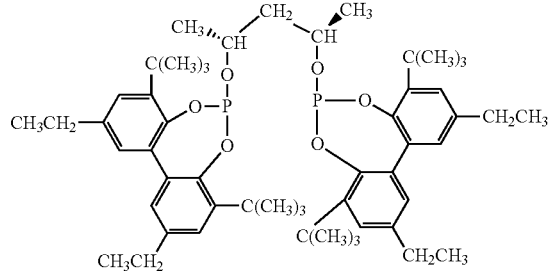

(2R,4R)-di[2,2'-(3,3'-di-tert-butyl-5,5'-dimethoxy-1,1'-biphenyl)]-2,4-pentyldiphosphite having the formula:

Ligand K

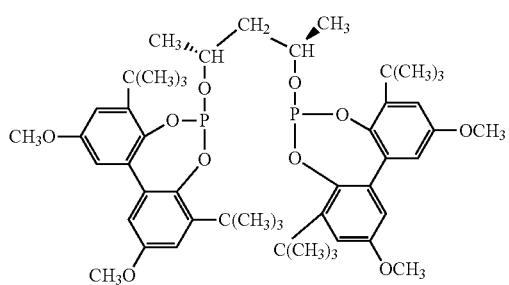

6-[[2'-[(4,6-bis(1,1-dimethylethyl)-1,3,2-benzodioxaphosphol-2-yl)oxy]-3,3'-bis(1,1-dimethylethyl)-5,5'-dimethoxy[1,1'-biphenyl]-2-yl]oxy]-4,8-bis(1,1-dimethylethyl)-2,10-dimethoxydibenzo[d,f][1,3,2]dioxaphosphepin having the formula:

6-[[2'-[1,3,2-benzodioxaphosphol-2-yl)oxy]-3,3'-bis(1,1-dimethylethyl)-5,5'-dimethoxy[1,1'-biphenyl]-2-yl]oxy]-4,8-bis(1,1-dimethylethyl)-2,10-dimethoxydibenzo[d,f][1,3,2]dioxaphosphepin having the formula:

Ligand M

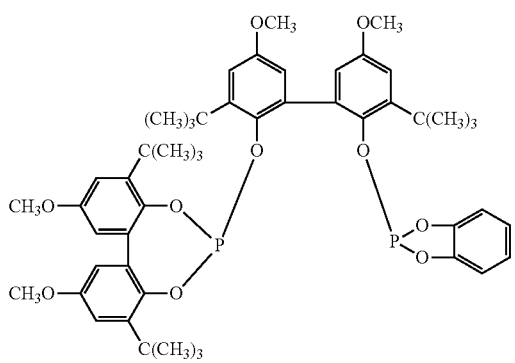

6-[[2'-[(5,5-dimethyl-1,3,2-dioxaphosphorinan-2-yl)oxy]-3,3'-bis(1,1-dimethylethyl)-5,5'-dimethoxy[1,1'-biphenyl]-2-yl]oxy]-4,8-bis(1,1-dimethylethyl)-2,10-dimethoxydibenzo[d,f][1,3,2]dioxaphosphepin having the formula:

Ligand N

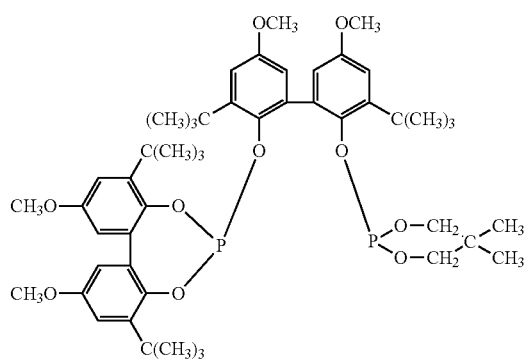

Ligand L

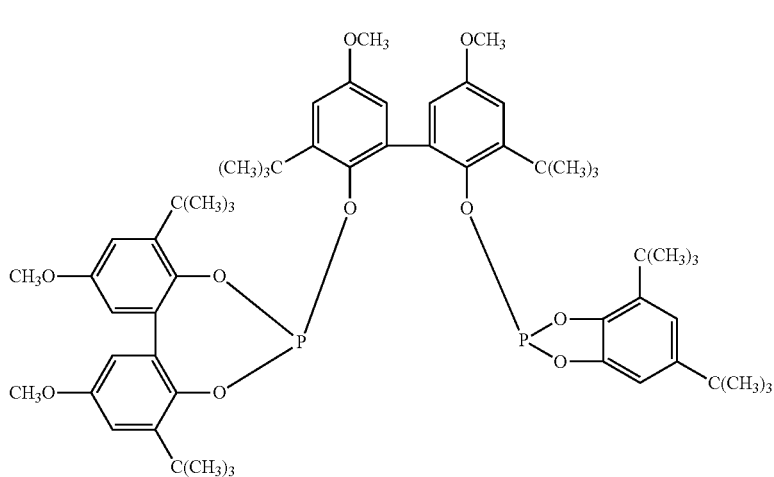

Examples of singly open ended organobisphosphite ligands include the following: 2'-[[4,8-bis(1,1-dimethylethyl)-2,10-dimethoxydibenzo[d,f][1,3,2]-dioxaphosphepin-6-yl]oxy]-3,3'-bis(1,1-dimethylethyl)-5,5'-dimethoxy[1,1'-biphenyl]-2-yl bis(4-hexylphenyl)ester of phosphorous acid having the formula:

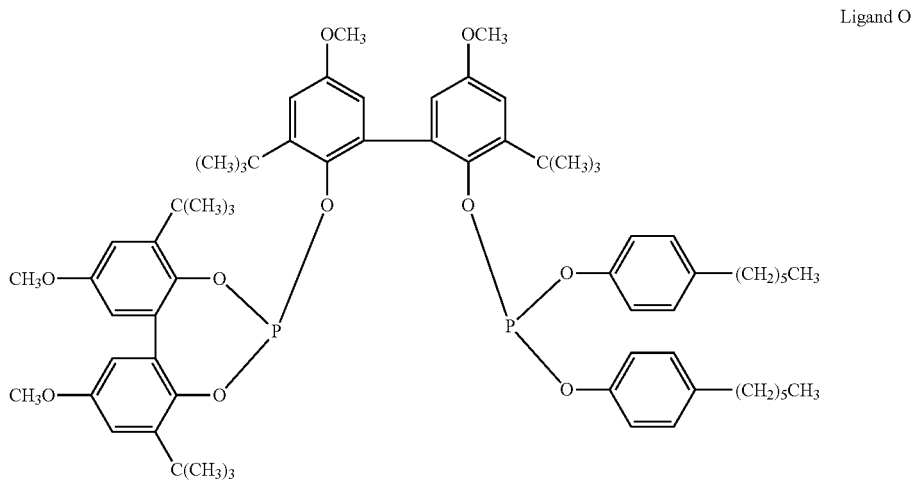

Ligand O

2-[[2-[[4,8,-bis(1,1-dimethylethyl), 2,10-dimethoxy-dibenzo-[d,f][1,3,2]dioxophosphepin-6-yl]oxy]-3-(1,1-dimethylethyl)-5-methoxyphenyl]methyl]-4-methoxy, 6-(1,1-dimethylethyl)phenyl diphenyl ester of phosphorous acid having the formula:

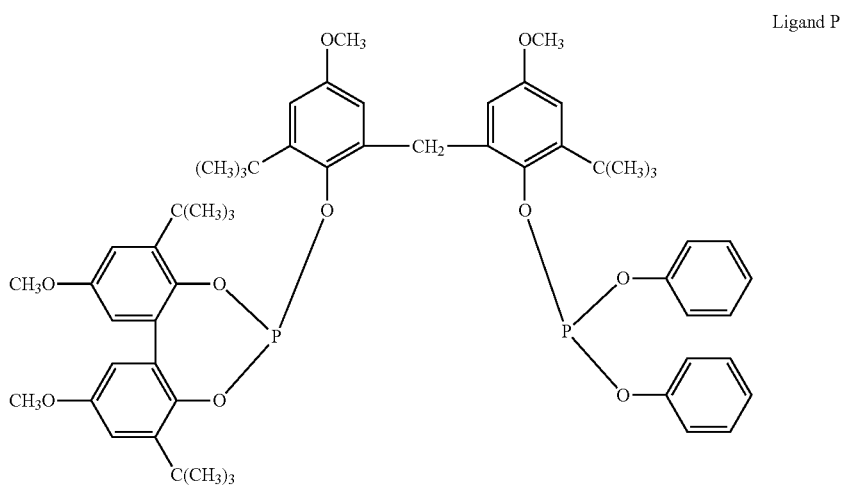

Ligand P

Examples of doubly opened organobisphosphite ligands include the following:

3-methoxy-1,3-cyclohexamethylene tetrakis[3,6-bis(1,1-dimethylethyl)-2-naphthalenyl]ester of phosphorous acid having the formula:

Ligand Q

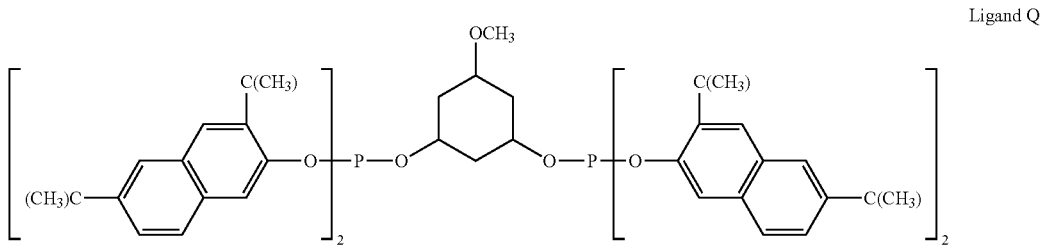

2,5-bis(1,1-dimethylethyl)-1,4-phenylene tetrakis[2,4-bis(1,1-dimethylethyl)phenyl]ester of phosphorous acid having the formula:

Ligand R

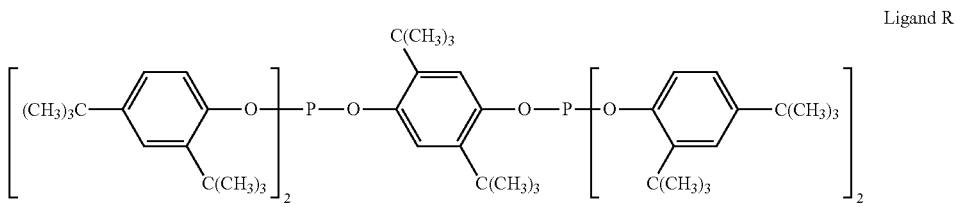

methylenedi-2,1-phenylene tetrakis[2,4-bis(1,1-dimethylethyl)phenyl]ester of phosphorous acid having the formula:

Ligand S

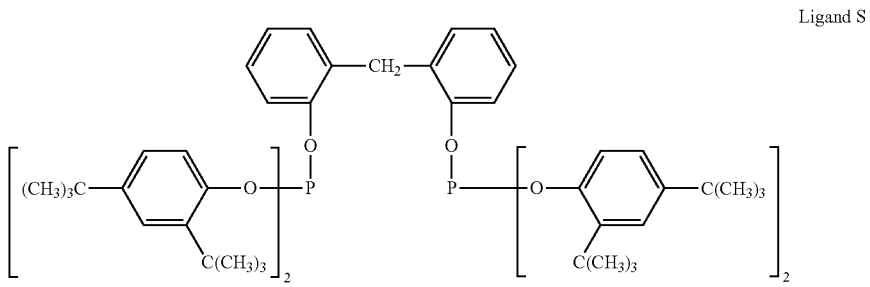

[1,1'-biphenyl]-2,2'-diyl tetrakis[2-(1,1-dimethylethyl)-4-methoxyphenyl]ester of phosphorous acid having the formula:

Ligand T

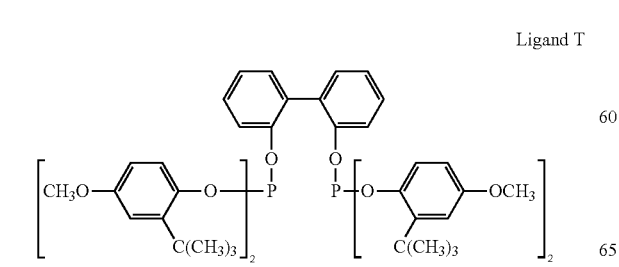

In a more preferred embodiment, illustrative examples of doubly open-ended organobisphosphite ligands include the following:

(VIII)

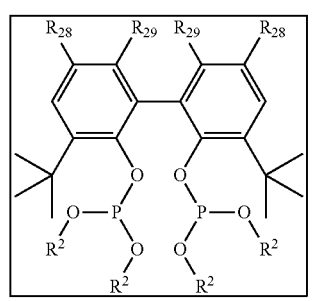

where $R^2$ is as defined above, and each $R_{28}$ independently may be a $C_{1-20}$ alkyl radical or an alkoxy radical; each $R_{29}$ independently may be a hydrogen atom, a $C_{1-20}$ alkyl radical or an alkoxy radical.

In a most preferred embodiment, the doubly open-ended organobisphosphite ligand is Ligand U:

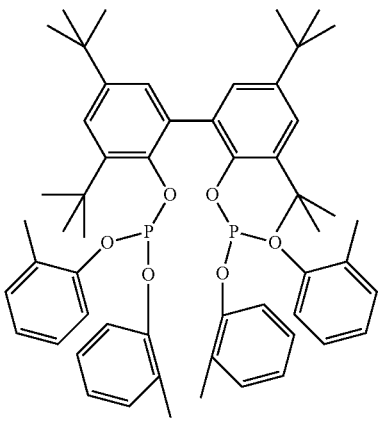

Ligand U

The organomonophosphite employable in the process of this invention comprises any organic compound comprising one phosphite group. Representative organomonophosphites include those having the formula:

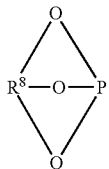

(IX)

wherein $R^8$ represents a substituted or unsubstituted trivalent hydrocarbon radical containing from 4 to 40 carbon atoms or greater, such as trivalent acyclic and trivalent cyclic radicals, e.g., trivalent alkylene radicals such as those derived from 1,2,2-trimethylolpropane, or trivalent cycloalkylene radicals, such as those derived from 1,3,5-trihydroxycyclohexane. Such organomonophosphites may be found described in greater detail, for example, in U.S. Pat. No. 4,567,306, the disclosure of which is incorporated herein by reference.

Representative diorganophosphites may include those having the formula:

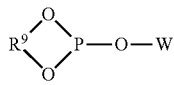

(X)

wherein $R^9$ represents a substituted or unsubstituted divalent hydrocarbon radical containing from 4 to 40 carbon atoms or greater and W represents a substituted or unsubstituted monovalent hydrocarbon radical containing from 1 to 18 carbon atoms.

Representative substituted and unsubstituted monovalent hydrocarbon radicals represented by W in the above formula include alkyl and aryl radicals, while representative substituted and unsubstituted divalent hydrocarbon radicals represented by $R^9$ include divalent acyclic radicals and divalent aromatic radicals. Illustrative divalent acyclic radicals include, for example, alkylene, alkylene-oxy-alkylene, alkylene-$NX^2$-alkylene, wherein $X^2$ is hydrogen or a substituted or unsubstituted hydrocarbon radical, alkylene-S-alkylene, and cycloalkylene radicals. The more preferred divalent acyclic radicals are the divalent alkylene radicals, such as disclosed more fully, for example, in U.S. Pat. No. 3,415,906 and U.S. Pat. No. 4,567,302, the disclosures of which are incorporated herein by reference. Illustrative divalent aromatic radicals include, for example, arylene bisarylene, arylene-alkylene, arylene-alkylene-arylene, arylene-oxy-arylene, arylene-$NX^2$-arylene, wherein $X^2$ is as defined above, arylene-S-arylene, and arylene-S-alkylene. More preferably, $R^9$ is a divalent aromatic radical, such as disclosed more fully, for example, in U.S. Pat. No. 4,599,206 and U.S. Pat. No. 4,717,775, the disclosures of which are incorporated herein by reference.

Representative of a more preferred class of diorganomonophosphites are those of the formula:

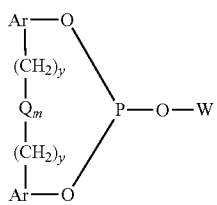

(XI)

wherein W is as defined above, each Ar is the same or different and represents a substituted or unsubstituted divalent aryl radical, each y is the same or different and has a value of 0 or 1, Q represents a divalent bridging group selected from $-C(R^{10})_2-$, $-O-$, $-S-$, $-NR^{11}-$, $-Si(R^{12})_2-$ and $-CO-$, wherein each $R^{10}$ is the same or different and represents hydrogen, alkyl radicals having from 1 to 12 carbon atoms, phenyl, tolyl, and anisyl, $R^{11}$ represents hydrogen or an alkyl radical of from 1 to 10 carbon atoms, preferably, methyl, each $R^{12}$ is the same or different and represents hydrogen or an alkyl radical having from 1 to about 10 carbon atoms, preferably, methyl, and m has a value of 0 or 1. Such diorganomonophosphites are described in greater detail, for example, in U.S. Pat. No. 4,599,206, U.S. Pat. No. 4,717,775, and U.S. Pat. No. 4,835,299, the disclosures of which are incorporated herein by reference.

Representative triorganomonophosphites may include those having the formula:

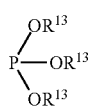

(XII)

wherein each $R^{13}$ is the same or different and is a substituted or unsubstituted monovalent hydrocarbon radical, for example, an alkyl, cycloalkyl, aryl, alkaryl, or aralkyl radical, which may contain from 1 to 24 carbon atoms. Illustrative triorganomonophosphites include, for example, trialkylphosphites, dialkylarylphosphites, alkyldiarylphosphites, and triarylphosphites, such as, triphenylphosphite, tris(2,6-triisopropyl)phosphite, tris(2,6-di-tert-butyl-4-methoxyphenyl)

phosphite, as well as the more preferred tris(2,4-di-tert-butylphenyl)phosphite. The monovalent hydrocarbon radical moieties themselves may be functionalized with the proviso that said functional groups do not significantly interact with the transition metal or otherwise inhibit hydroformylation. Representative functional groups include alkyl or aryl radicals, ethers, nitriles, amides, esters, $-N(R^{11})_2$, $-Si(R^{12})_3$, phosphates, and the like, wherein $R^{11}$ and $R^{12}$ are defined hereinbefore. Such triorganomonophosphites are described in more detail in U.S. Pat. No. 3,527,809 and U.S. Pat. No. 5,277,532, the disclosures of which are incorporated herein by reference.

In addition to the metal-ligand complex catalyst, free ligand (i.e., ligand that is not complexed with the metal) may also be present in the reaction zone, and preferably is physisorbed on the support. The free ligand may correspond to any of the aforementioned organophosphite ligands. The hydroformylation process of this invention may involve from about 0.1 moles or less to about 100 moles or more, of free ligand per mole of metal. Preferably the hydroformylation process of this invention is carried out in the presence of from about 1 to about 50 moles of ligand, and more preferably from about 1.1 to about 4 moles of ligand, per mole of catalytic metal; said amounts of ligand being the sum of both the amount of ligand that is bound (complexed) to the metal present and the amount of free (non-complexed) ligand present. If desired, make-up or additional ligand can be supplied to the support at any time and in any suitable manner, e.g. to maintain a predetermined amount of free ligand.

Any of the organopolyphosphite ligands, including preferred organobisphosphite ligands, which are described hereinbefore may be subjected to oxidation such that all but one of the phosphorus (III) atoms is converted into phosphorus (V) atoms. The resulting oxidized ligand can comprise an organomonophosphite-polyphosphate or, preferably, an organomonophosphite-monophosphate, which suitably is employed in at least a 2/1 molar excess relative to transition metal so as to provide for the organomonophosphite ligand component of this disclosure.

The amount of metal-ligand complex(es) present in the hydroformylation process of this disclosure need only be that minimum amount necessary to catalyze the desired hydroformylation process. Generally, in the hydroformylation of propylene, the amount of metal, preferably, rhodium, is greater than about 0.001 wt % and preferably, greater than about 0.1 wt % of the catalyst (based on the dry weight of metal plus dry weight of support). The amount of metal is preferably less than 15 wt % of the catalyst and is preferably less than 1 wt %. For $C_4+$ olefins, such as butene and those of higher molecular weights, the suitable amount of metal may be higher, because higher olefins exhibit reduced activity as compared with propylene. While, the powdered form (e.g., up to 100% metal-ligand complex) of the Rh-ligand complex can be used, this is generally too expensive to be economically feasible and the solid may not be strong enough to endure the physical abuse inherent in a solid state heterogeneous catalyst application, thus supported catalysts are preferred. Since rhodium is a very expensive metal, the amount of catalyst is generally kept to a minimum, and other parameters such as temperature may be adjusted to obtain the desired reactivity, as is known to those skilled in the art.

Both the organopolyphosphite and the organomonophosphite ligand employable in the process of this disclosure, including free and complexed forms, are provided to the process in a quantity such that the molar ratio of each ligand to the transition metal is at least 2 equivalents of P(III) atom per equivalent of transition metal. Preferably the quantity of each ligand is at least 2.5 moles per mole of transition metal but preferably less than 10 moles and even more preferred, less than 4 equivalents P(III) per equivalent of transition metal. Alternatively, if solid ligand (such as an ionic ligand salt) is also used as the support, there is no upper limit to the ratio of ligand to catalytic metal.

The amount of transition metal, organopolyphosphite ligand, and organomonophosphite ligand can be readily determined by well known analytical methods. From these analyses, the required molar ratios can be readily calculated and tracked. The amount of transition metal, preferably rhodium, is best determined by atomic absorption or inductively coupled plasma (ICP) techniques. The presence and amount of ligands can be analyzed by $^{31}P$ nuclear magnetic resonance spectroscopy (NMR) or by high pressure liquid phase chromatography (HPLC). This is possible since the complex is readily dissolved off the support with conventional solvents such as tetrahydrofuran (THF) or toluene. Ionic ligands may require an aqueous solvent.

It has been found that additional ligand can be added to the gas phase reaction zone to replace ligand that has decomposed such as, for example, by hydrolysis or oxidation. The amount of organophosphite ligand on the support can be increased or maintained at any time during the continuous hydroformylation process in any suitable manner such as, for example, by adding a quantity of organophosphite ligand continuously or intermittently such as, for example, in a carrier liquid feed to the catalyst bed.

The preferred carrier liquid for the organophosphorous ligand is the aldehyde product. Other suitable carrier liquids include volatile organic compounds, such as THF or toluene, which will readily evaporate upon resumption of reaction depositing the ligand on the support. Mixtures of carrier liquids can be employed. In the current invention, the organophosphite ligand can readily be reintroduced and spontaneously forms into the metal-ligand complex in the time that it takes to evaporate the carrier liquid used to introduce it.

The amount of rhodium can be increased as needed by the same means that ligand additions are performed if the initial rhodium charge is found to be insufficient.

The supports used in this invention are solid particulate materials that are inert under the hydroformylation reaction conditions used. The support can be selected from support materials such as, for example, silica, gamma alumina, titania, zirconia, alumina silicates, clays, and activated carbon. Mixed composite supports in which a high surface area support is deposited over a lower surface area support may also be used. The surface area of the support does not appear to be critical; thus, supports within a wide range of surface areas, e.g., at least about 1 square meter per gram or higher (as determined by BET) will suffice. Silica is the preferred inorganic support.

The carbon supports employed in the present invention are well known in the art. Activated, non-graphitized carbon supports are preferred. These supports are characterized by high adsorptive capacity for gases, vapors, and colloidal solids and relatively high specific surface areas.

The hydroformylation process of this disclosure may be asymmetric or non-asymmetric, the preferred process being non-asymmetric; and may be conducted in any fashion, including continuous, semi-continuous, or batch processes. As used herein, the term "hydroformylation" is contemplated to include all operable asymmetric and non-asymmetric hydroformylation gas phase processes that involve converting one or more substituted or unsubstituted olefinic compounds to one or more substituted or unsubstituted aldehydes.

The particular reaction conditions are not narrowly critical and can be any effective reaction conditions sufficient to produce at least one desired product. The exact reaction conditions will be governed by the best compromise between achieving high catalyst selectivity, activity, lifetime and ease of operability, as well as the intrinsic reactivity of the starting materials in question and the stability of the starting materials and the desired reaction product to the reaction conditions.

For purposes of this invention, GHSV is gas hourly space velocity, which is the rate of gas flow over the catalyst. It is determined by dividing the volume of gas (at 25° C. and 1 atmosphere) that passes over the catalyst in one hour by the volume of the catalyst (liters of feedstock/hr/liter of catalyst). The GHSV can vary significantly, depending upon a variety of factors such as, for example, reaction conditions, composition of the feedstock and quantity and type of catalyst being used. The GHSV can be maintained at any rate in the range of from about 1 to about 30,000 hr$^{-1}$ or more, preferably will be maintained at a rate of at least about 500 hr$^{-1}$, and more preferably will be maintained at a rate of at least 1,000 hr$^{-1}$.

In general, the hydroformylation process of this disclosure can be conducted at any operable reaction temperature. The temperature in the reaction zone is selected from the range of from about 15° C. to about 200° C., preferably a temperature in the range of from about 50° C. to about 150° C., with an especially preferred temperature in the range of from about 75° C. to about 125° C. In one embodiment the process temperature is greater than about −25° C. and less than about 200° C.

In general, the hydroformylation process of this disclosure can be conducted at any operable reaction pressure. Generally, the total gas pressure comprising hydrogen, carbon monoxide and olefinic starting compound may range from about 1 psia (6.9 kPa) to about 10,000 psia (68.9 MPa). In general, however, it is preferred that the process be operated at a total gas pressure of hydrogen, carbon monoxide and olefin starting compound of less than about 2,000 psia (613.8 MPa) and more preferably less than about 500 psia (3.4 MPa). More specifically the carbon monoxide partial pressure of the hydroformylation process of this invention may vary from about 1 psia (6.9 kPa) to about 1000 psia (6,890 kPa), and more preferably from about 3 psia (20.7 kPa) to about 800 psia (5,516 kPa), and even more preferably, from about 20 psia (137.8 kPa) to about 100 psia (689 kPa); while the hydrogen partial pressure is preferably about 5 psia (34.5 kPa) to about 500 psia (3,450 kPa), and more preferably from about 10 psia (68.9 kPa) to about 300 psia (2,070 kPa). In one embodiment the total gas pressure comprising carbon monoxide, hydrogen, and olefinic reactant(s) is greater than about 25 psia (173 kPa) and less than about 2,000 psia (13,800 kPa).

The hydroformylation reaction may be carried out in a tubular reactor using a fixed bed of the catalyst. The reactants may be fed to the catalyst by feeding down or up or at any other non-vertical angle, or a combination of these, to a fixed bed located in a tubular reactor. It may be desirable to use a reactor design that operates by plug flow and causes minimal turbulence in the reactor zone. The hydroformylation reaction may be effected in a dynamic bed of the catalyst. In such a reaction, the bed of catalyst is moving such as in the case of a fluid bed of the catalyst.

Where the olefin reactant is a higher boiling material not easily vaporized, it can be diluted with a lower boiling non-reactive solvent or diluent and thus transported over the solid catalyst in the vapor phase. The degree of dilution in some cases can be quite extreme and of course, such conditions will adversely affect the cost of hydroformylation. Suitable solvents and diluents include aliphatic and aromatic hydrocarbons, water vapor, esters, non-condensable ketones, and the like.

Water vapor, either in a continuous and/or intermittent manner, is contacted with the catalyst under reaction conditions. In one embodiment, water is present in an amount that is sufficient to substantially maintain the activity of the reaction. Without intending to be limited by theory, it is thought the water vapor aids in decomposing partially decomposed ligand fragments that act as catalyst inhibitors or poisons. The water vapor can be introduced in several ways, such as passing one or more of the feed streams through a water-containing vessel (such as a bubbler), or by injecting steam directly into the reaction zone or into one or more of the feed streams upstream of the catalyst. The amount of water is not thought to be critical except that it is preferred that the resulting feeds to the catalyst are be above the dew point in the reactor and it is preferred that the amount be sufficient to hydrolyze the impurities on the catalyst.

The minimum amount of water needed for a batch mode process can be estimated by multiplying the amount of water per hour being fed to the catalyst (in moles/hr) by the number of hours the water is present, and comparing that value to the number of moles Rh present in the catalyst bed. The number of moles of water advantageously is at least 0.001 times the moles of Rh, and can be at least 0.01 times, can be at least 0.1 times, and more preferably is at least equal to the number of moles of Rh. In one embodiment, in a continuous operation wherein water is continuously present, the amount of water advantageously is equal to or exceeds the amount of ligand degradation on a mole-to-mole basis. Depending on the molecular weight of the ligand, typical organophosphite ligand degradation rates are less than 0.6 grams of ligand/liter of supported catalyst/day, preferably less than 0.1 grams of ligand/liter of supported catalyst/day, and most preferably less than 0.06 grams of ligand/liter of supported catalyst/day under normal hydroformylation conditions. Excess water vapor acts as a diluent stream that generally has no significant negative impact on the process since in most cases much larger amounts of inert gases are already present. However, it is preferred to avoid excessive amounts of water that could condense into liquid. This is readily accomplished by saturating only one feed stream at ambient temperature such that upon heating up and/or being diluted with other feed streams, the resulting combined feed stream is well above the dew point temperature.

If the feed stream does not contain sufficient water for the hydrolysis, then activity decline may be observed. An additional amount of water vapor can then be added to restore activity. Depending on operating conditions, the water feed may be pulsed or varied depending on the feed stream conditions (i.e., more or less olefin is present). Should raw materials (olefin or syn gas) contain sufficient water under normal operations, added water vapor may not be needed but changes or variation in raw material quality may necessitate auxiliary amounts of water being added to maintain catalyst activity.

When the feed stream is a vent stream of a conventional liquid phase hydroformylation reactor wherein the vent stream contains unreacted olefin, syn gas, inert gases (alkanes, $N_2$, etc.) as well as aldehyde vapors, it may contain water vapor from a number of sources such as raw materials, catalyst recovery and treatment technologies (U.S. Pat. No. 6,307,110, U.S. Pat. No. 5,183,943, U.S. Pat. No. 5,741,942), and aldol condensation reactions (U.S. Pat. No. 4,148,830). New liquid phase reactor catalyst solutions may not contain sufficient amounts of water; thus, auxiliary water will need to be added at first until a steady-state amount of water vapor in the purge vent of the liquid phase reactor is established.

The hydroformylation process of the present disclosure may be used on other process vent streams, such as vent streams from carbonylation or hydrogenation reactors, where it would have similar advantages to recover reactant value from otherwise wasted olefin-containing streams.

In one embodiment, the catalyst is contacted with a buffer, preferably an aqueous buffer. Advantageously, the buffer is contacted with the catalyst after the reaction is stopped. Without intending to be limited by theory, it is thought that the buffer removes phosphite decomposition species. These decomposition species act as catalyst inhibitors or poisons and, in addition, may catalyze the decomposition of additional phosphite ligand.

Examples of suitable buffers are described in U.S. Pat. No. 5,741,942 at col. 39, and include oxyacid salts (and mixtures thereof with the corresponding acid) such that the solution pH ranges from 3 to 9 (preferably from 4 to 8 and most preferably between 4.5 to 7.5). Representative buffer systems include mixtures of one or more anions selected from the group consisting of phosphate, phosphite, carbonate, citrate, and borate compounds and one or more cations selected from the group consisting of ammonium and alkali metals (e.g., sodium, potassium and the like). Preferred buffer systems comprise phosphate or citrate buffers. Mixtures of buffers can be employed. Optionally, organic nitrogen compounds may be added with or as part of the buffer solution to scavenge the acidic hydrolysis by-products formed upon hydrolysis of the organophosphate ligand as taught, for example, in U.S. Pat. No. 4,567,306 and U.S. Pat. No. 4,835,299. The preferred nitrogen compounds should be volatile and exhibit a pKa+/−3 pH units from the buffer solution. The buffer solution advantageously comprises water, or mixtures of water and polar organic solvents such as dimethylsulfoxide, N-methylpyrrolidone, or $C_1$-$C_{10}$ alcohols such as methanol, ethanol, propanol, butanol, pentanol, and hexanol or mixtures thereof. It is desired that the buffer solution treatment be done with ligands and catalysts that have marginal (if any) solubility in the buffer solvent to prevent ligand and catalyst leaching. Common ion effect buffers can help reduce leaching. In addition, highly concentrated buffer solutions may minimize the amount of catalyst leaching. The preferred ligands for the buffer treatment are those with very low (less than 1 ppm) water solubility (as can readily be determined by gas chromatography or high pressure liquid chromatography as described in *OECD Guidelines for Testing of Chemicals*, Vol. 105, "Water Solubility," Jul. 27, 1995).

The frequency of buffer treatment is dependant upon the rate of ligand decomposition, the amount of ligand present at the beginning of the process, the support surface area, and other factors specific to the application of the technology. Fortunately, there are several indicators that a buffer wash is needed. An activity decline despite adequate water vapor contact is an indication that substantial amounts of ligand degradation have been generated and that these degradation products need to be removed to improve or restore activity. Without intending to be limited by theory, it is thought that the degradation products eventually build up, thereby blocking active catalytic sites, plugging support pores, and/or acting as weak catalyst inhibitors. Another indication can be gleaned from a calculation based on the ligand degradation rate described above. Buffer treatment can be initiated based on such calculations that predict when a specified amount of ligand should have decomposed, thus potentially blocking active sites or otherwise interfering with catalysis. As a first approximation, the ligand degradation rate in liquid-phase catalysis using the same ligand can be used to estimate the rate of ligand degradation in the present gas phase process, assuming similar reaction temperatures. With either method, operating experience may lead to a routine treatment on a regularly scheduled basis to maintain desired performance, much like any other preventative maintenance practice.

The buffer treatment is typically of a short duration, and is advantageously a few hours at most. The treatment is preferably done at less than 100° C., more preferably less than 70° C., and most preferably less than 40° C. The treatment can be done in batch mode or as a continuous flush. The amount of buffer advantageously is sufficient to neutralize the acid impurities present on the catalyst. Completion of buffer treatment is most conveniently determined by measuring the pH of the buffer before and after treatment. A pH drop of less than 0.5 pH units (preferably less than 0.1 pH units) indicates that most of the acid impurities have been removed. Larger pH drops suggest further flushes or more batch mode treatments are needed. The pH drop is also dependant on the buffer concentration, but generally buffer concentrations of 0.001 to 0.5 molar in the buffer feed solution are preferred. Optionally, a water wash is performed after the buffer treatment to remove residual salts. All buffer and water washes should be de-aerated (free of $O_2$ or peroxides) to prevent ligand oxidation. The treatment can be done at operating pressures or, more conveniently, at atmospheric pressure under inert gas (e.g., $N_2$) or syn gas.

When the present process is used on the exit purge vent stream of a conventional liquid phase hydroformylation reaction zone, the feed to the vapor phase reactor (defined hereinafter as "reaction gas" or "reaction product gas") is contemplated to include, but is not limited to, a reaction mixture comprising at least one aldehyde product formed in the reaction and, optionally, unconverted reactants including unreacted olefin, carbon monoxide, and/or hydrogen.

It is to be understood that, in addition to the reaction products and starting materials, the hydroformylation reaction gas exiting the gas phase reactor and/or the liquid phase reactor may contain minor amounts of additional compounds, such as those that have either been deliberately added or formed in situ during the process. Examples of such additional ingredients may include water, catalyst solvents, and in situ formed products, such as saturated hydrocarbons, and/or unreacted isomerized olefins corresponding to the olefin starting materials, and/or high boiling aldehyde condensation byproducts, and/or one or more degradation products of the catalyst and/or organophosphite ligands, including by-products formed by hydrolysis of the organophosphite ligands.

Depending on the composition of the vent stream, it may be necessary to add additional carbon monoxide or hydrogen to maintain the required stoichiometry to convert the available olefin to product. Optionally, it may be desirable to have a knock out pot, de-mister, or condenser upstream of the vapor phase reactor to remove condensables (or entrained liquids) from the liquid phase reactors. An upstream gas compressor to increase the vent stream pressure entering the vapor phase hydroformylation reactor may also be desirable in that increased reaction rates are usually observed at higher pressure.

Recovery and purification of desired products may be accomplished by any appropriate means. The desired products of the process of this disclosure may be recovered in any conventional manner, and one or more separators or separation zones may be employed in any given process to recover the desired reaction product from its crude reaction product. Suitable separation and purification methods include, for example, condensation from the vapor phase, distillation, phase separation, extraction, absorption, crystallization, membrane methods, derivative formation and the like.

In one embodiment, the aldehyde product in the vapor phase is sent to a vapor phase hydrogenation reactor to convert the aldehyde to at least one alcohol. This may be done with or without purification of the aldehyde product between reactors.

Specific Embodiments of the Invention

The process of this disclosure will be further clarified by a consideration of the following examples, which are intended to be purely exemplary of the use of the invention. Other embodiments of the disclosure will be apparent to those skilled in the art from a consideration of this specification or practice of the process as disclosed herein.

In the examples that follow, reaction rate is reported as pounds of aldehyde produced per bulk cubic foot of catalyst per hour (lb/ft$^3$ cat-hr), and gas flow rates are reported in standard liters per hour (SLH). The purities of olefin feeds are greater than 99.8 percent. All parts and percentages are by weight unless otherwise indicated.

General Hydroformylation Process Procedure

Procedure A: The reaction is carried out in a vapor phase reactor consisting of 316 stainless steel u-tube or a glass tube. The tube is heated in a thermally controlled oil bath. The reaction system is computer controlled and capable of unattended 24 hour operation. $H_2$, CO, olefin and $N_2$ are independently fed to the reactor. The downflow side of the reactor is packed with glass beads and serves as a preheater. The catalyst is located at the beginning of the upflow section of the reactor. The catalyst volume is 1.5 ml. The remainder of the tube is filled with glass beads. The product stream exiting the reactor is maintained in the gas phase and is fed to an online gas chromatograph (GC) where the stream is analyzed. The only compounds observed in the product mixture are unreacted feed, iso-aldehyde, and normal-aldehyde. There is no indication of saturated hydrocarbons or aldol condensation products.

Procedure B: The reactor is a 120 ml Fisher Porter™ tube equipped with an inlet line for the gaseous feeds and an outlet line for the product stream. The inlet line extends to the bottom of the tube and ends with a sparger. The reaction tube is heated in a thermally controlled oil bath. The reaction system is computer controlled and capable of unattended 24 hour operation. $H_2$, CO, olefin and $N_2$ are independently fed to the reactor. The product stream exiting the reactor is maintained in the gas phase and is fed to an online GC where the stream is analyzed. The reaction tube is first loaded through an open top port with glass beads to just above the inlet gas sparger followed by addition of 1.00 g (2.5 ml) of support. The reactor is then placed in an oil bath and attached to the reactant inlet and product outlet lines of the glass reactor system. Under a nitrogen purge the catalyst solution is added via syringe to the support bed. An attempt is made to cover as much of the support bed as possible with the catalyst solution. Syn gas ($H_2$:CO=1:1, 100 psig) flow is started and the system is heated to 70° C. and maintained for 2 hours activation. Olefin flow is then started.

The catalyst is washed in the following way: (1) the olefin feed is stopped and $H_2$:CO is adjusted to 1:1 (100 psig); (2) sodium phosphate buffer solution (0.08 molar) with pH=6.71 is added via syringe completely covering the catalyst bed/glass beads; (3) syn gas is sparged through the liquid for 10 minutes and then as much liquid as possible is removed by syringe. The syn gas flow is maintained for 2 hours and then the olefin feed is restarted and syn gas ratio readjusted back to the previous values. Ligand is added in the following way. The olefin is stopped and $H_2$:CO adjusted to 1:1 (100 psig). A THF solution containing 1.5 equivalents of the ligand to the previously charged rhodium is added to the catalyst bed via syringe. The syn gas flow is maintained for 2 hours and then the olefin is restarted and syn gas ratio readjusted to hydroformylation conditions.

Example 1

Rh=0.5 wt %

The catalyst is prepared in the following way. In a $N_2$ dry box 0.0267 g Rh(CO)$_2$AcAc and 0.0865 g of Ligand D (Ligand D:Rh=1) is dissolved in 1.5 ml tetrahydrofuran (THF). This solution is added in one step to 2.04 g of 10-20 mesh KA-160, a commercially available silica. The mixture is gently shaken and then brought out of the dry box in a sealed vial and is rolled for about ½ hr. The catalyst contains 0.5 wt % rhodium. Then, 0.760 g (1.5 ml) of the catalyst is charged to a reactor tube. The catalyst is "activated" by heating in $H_2$:CO=1:1 at 70° C. for 2 hours at 100 psig. The flow rate is about 10 SLH.

After this time propylene is added and the flows are adjusted to propylene=6.74 SLH, $H_2$=2.6 SLH, and CO=1.60 SLH, following Procedure A with pressure at 80 psig and temperature at 70° C. The catalyst is initially hyperactive with a total aldehyde activity occurring at about 6 hr into the run at 119.3 lb/ft$^3$ cat-hr and the ratio of normal to iso products (n/i)=26.9. Within 48 hours the activity declines to 35 lb/ft$^3$ cat-hr. The temperature is decreased to 60° C., resulting in smooth operation with the total aldehyde activity@17 lb/ft$^3$-cat hr for one week. During this time the n/i remains relatively constant at 29.

While not wishing to be bound by any theory, the initial hyperactivity is thought to be the activity before the formation of any decomposition or degradation products that are poisonous to the catalyst, and the decline in activity is thought to be due to the buildup of such catalyst poisons. The activity levels off at that point wherein in-situ generated water from the aldol reactions (and impurities from feeds) decomposes the poisons at the same rate they are formed.

Example 2

Rh=0.125 wt %

Example 1 is repeated except that the amount of rhodium is 0.125 wt %, the ratio of Ligand D:Rh=1.5, and the initial run conditions are 50° C. and 50 psig. The catalyst activity peaks at an aldehyde production of 59.2 lb/ft$^3$ cat-hr and n/i of 60 after 48 hours. The activity declines and then remains relatively stable for 200 hours at 21.7 lb/ft$^3$ cat-hr. The n/i is essentially constant.

Example 3

Rh=0.06 wt % and Water Saturated Syn Gas

Example 1 is repeated except that the amount of rhodium is 0.06 wt %, the ratio of Ligand D:Rh=1.5 and the initial run conditions are 60° C. and 25 psig. The rate initially increases to 48 lb/ft$^3$ cat-hr then decreases to 31 lb/ft$^3$ cat-hr. The activity as a function of time is shown in FIG. 1. On Day 9, the syn gas is water saturated by passing it through water before it enters the reactor (previously the syn gas is dry). The activity

Example 4

Figure 2:
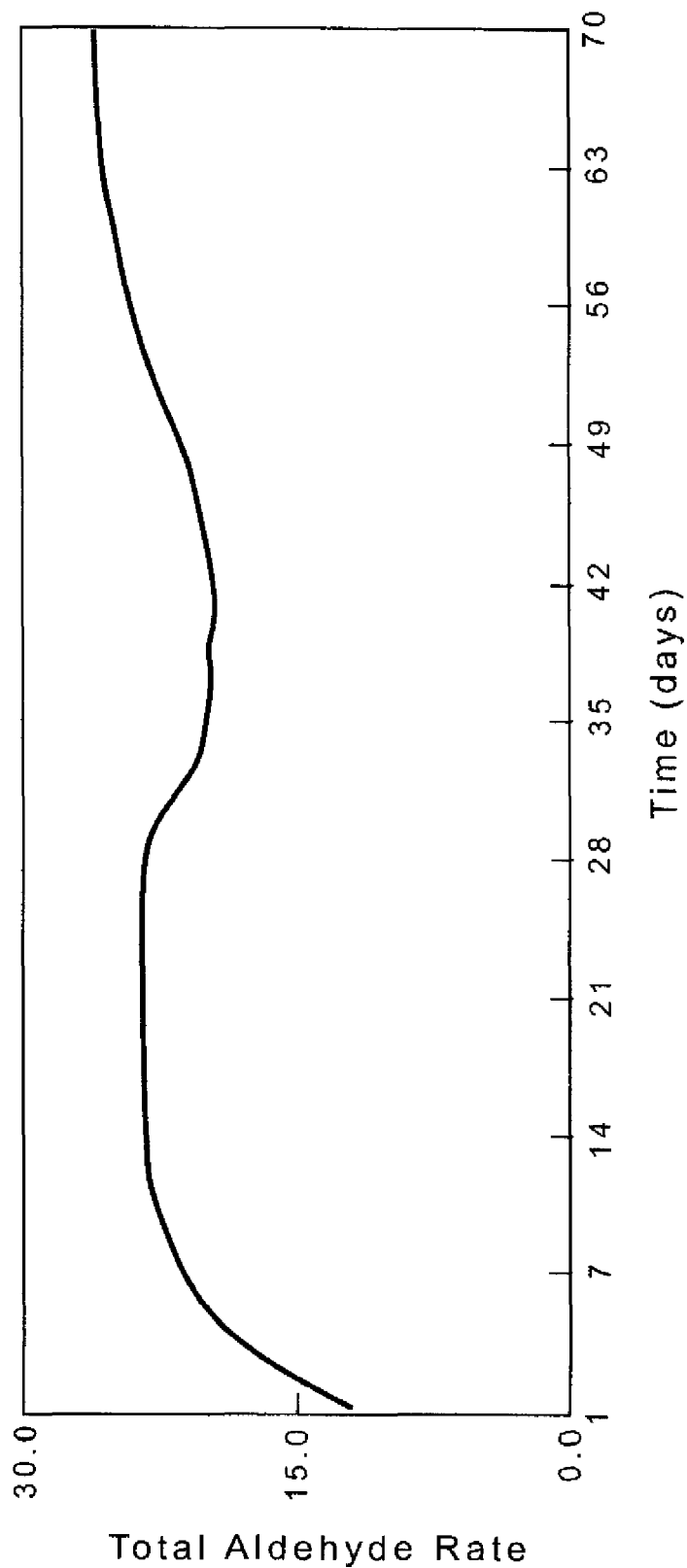
FIG. 2 is a plot of the rate of product formation expressed in $lb/ft^3$ cat-hr. as a function of on-stream time for Example 4.

A 0.125 wt % rhodium catalyst with Ligand U:Rh=1.5 is prepared as in Example 1 and initially is run using Procedure A at 60° C. and 25 psig. The catalyst is "activated" by heating under a $H_2$:CO=1:1 at 60° C. for 2 hours. The flow rate is about 10 SLH. Propylene is then added and the flows are adjusted to propylene=6.74 SLH, $H_2$=2.6 SLH, and CO 1.60 SLH. The activity as a function of time is shown in FIG. 2. The syn gas is not saturated with water from the beginning through 43 days. The catalyst activity gradually increases with time and levels off at 20.5 lb/ft$^3$ cat-hr (the initial rate increases represent residual catalyst activation). The n/i is 114 at these conditions. Starting on Day 39 all the feed rates are reduced by half. The activity and n/i drop slightly to 17.5 lb/ft$^3$ cat-hr and 100, respectively. On Day 42 water-saturated syn gas is started. The activity gradually increases up to 21 lb/ft$^3$ cat-hr through Day 70 and is higher than that of the initial catalyst even at ½ the flow rate.

Example 5

Procedure B

Figure 3:
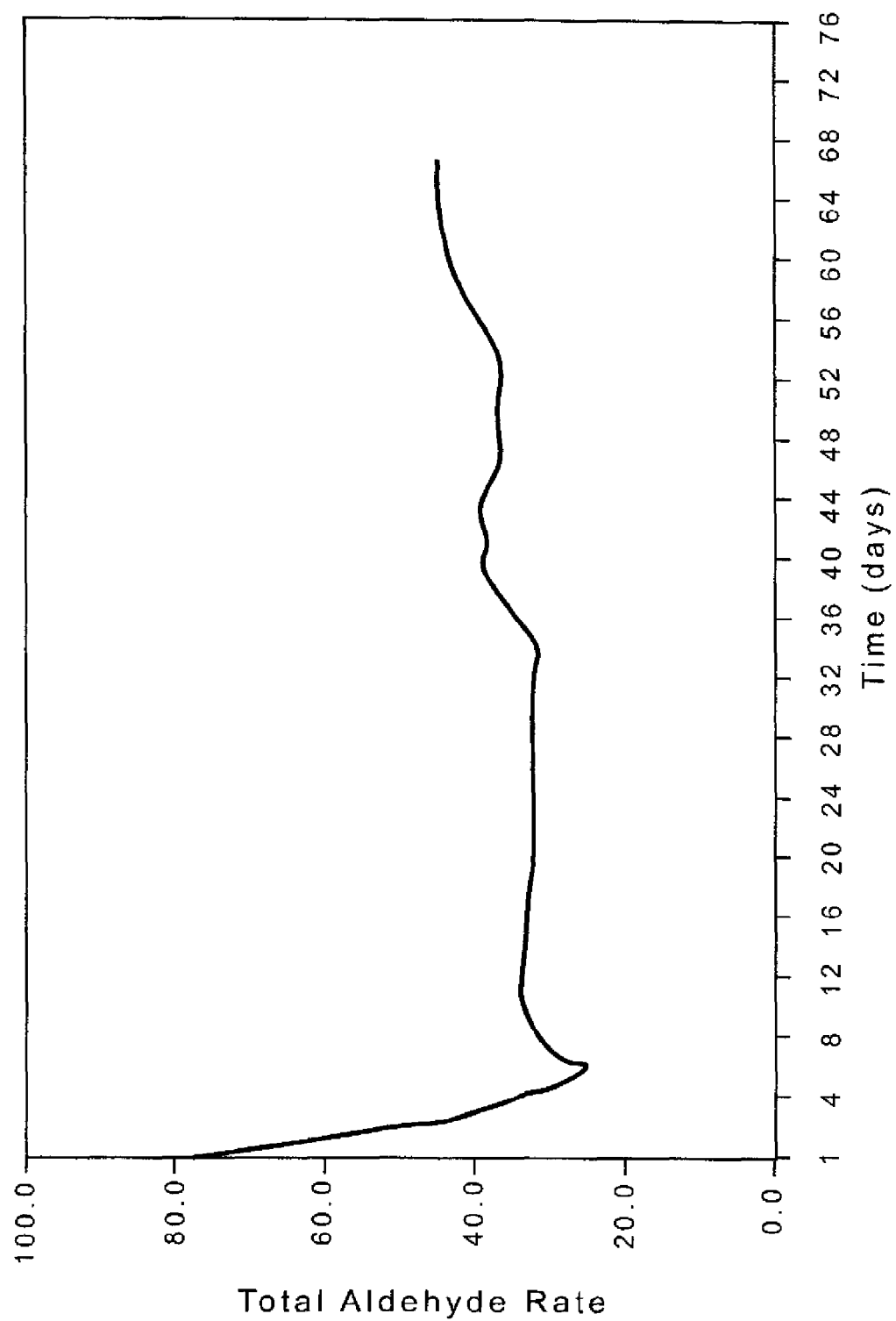
FIG. 3 is a plot of the rate of product formation expressed in $lb/ft^3$ cat-hr. as a function of on-stream time for Example 5.

The glass reactor tube is charged with glass beads to a level that is above the inlet gas feed sparger. Next, 10-20 mesh KA-160 is added as support and the reactor is sealed and put under $N_2$. Similar to Example 1, Ligand D and Rh(CO)$_2$AcAc (L:Rh=1.15) dissolved in THF is added by syringe to the KA-160; however, Procedure B is employed. The rhodium concentration is 520 ppm. The catalyst is activated in situ as in Example 1 prior to addition of propylene. The ligand is added to the catalyst during the course of the reaction. The catalyst is also washed, as described hereinbelow, with a buffer solution periodically during the run to reactivate it. The results are shown in FIG. 3. The run is started at 70° C., 100 psig, $H_2$=2.80 SLH, CO=1.60 SLH, and propylene=6.74 SLH. The syn gas is water saturated (note no residual catalyst activation period and the initial hyperactivity). On Day 4, 0.5 eq of Ligand D in THF is added to the catalyst. The activity levels off at 37.2 lb/ft3-cat hr and n/i ratio is 52. From Day 8 through Day 39 the activity is very constant.

The temperature is increased to 80° C. on Day 39. All other conditions remain the same. The activity increases to 40 lb/ft3-cat hr and n/i drops to 33.

Buffer wash 1.—On Day 42 the pressure is dropped to 1 atm and syn gas/propylene is shut off and $N_2$ is started. 4 ml of sodium phosphate buffer solution is added. The catalyst bed is covered with the solution. The buffer remains in place for 15 minutes and is then syringed off. The catalyst is reactivated for 2 hours at 80° C., 100 psig with $H_2$ and CO then the original flows are re-established. From Day 42 through 56 the reaction is maintained at these conditions. The activity is about 30 lb/ft$^3$-cat hr and the n/i=30.

Buffer wash 2.—On Day 57 another buffer wash is performed as described above. Reaction conditions are re-established and the reaction proceeds until Day 63. On Day 63 the activity is 42.4 lb/ft$^3$-cat hr and the n/i=38.

On Day 63 the temperature is increased to 100° C., all other conditions remaining the same. A buffer wash is carried out on Day 63 and again on Day 69. Stable activity is maintained with the routine buffer washes under these harsh conditions.

Example 6

A catalyst is prepared with a triorganophosphite ligand in the following way. All steps are carried out under $N_2$. 0.0033 g Rh(CO)2AcAc and 0.0818 g of tris(2,4-di-tert-butylphenyl)phosphite are dissolved in 1.419 g of tetraglyme. After gently heating, 1.374 g of this mixture is added to 2.001 g KA-160. This mixture is rolled for 0.5 hr. The resulting catalyst contains 354 ppm rhodium and the molar ratio of Ligand:Rh=10.

The catalyst is used to hydroformylate propylene as described in Example 5 under the following conditions: 80° C., 150 psig, $H_2$=1.44 SLH, CO=0.8 SLH, and propylene=1.86 SLH. After an initial break-in period, the aldehyde activity=15.5 lb/ft3 cat hr and the n/i=1.7. After 160 hr the activity=7.9 lb/ft3 cat hr and the n/i=1.7.

Example 7

A catalyst support is made from tris(2,4-di-tert-butylphenyl) phosphite in the following way. 3.64 g of tris(2,4-di-tert-butylphenyl)phosphite is mixed with 0.9 g starch and pressed for 1 hr a @17,000 psig in a die. The obtained solid pellet is crushed and sieved to 8-20 mesh. This support material is approximately 80% tris(2,4-di-tert-butylphenyl)phosphite and 20% starch. Under $N_2$, 0.0043 g Rh(CO)2AcAc and 0.0211 g of Ligand C are dissolved in 1.008 g of methanol. 0.913 g of this mixture is added to 2.003 g of the tris(2,4-di-tert-butylphenyl)phosphite/starch support. The material is well mixed and placed under a vacuum for 2 hours.

Figure 4:
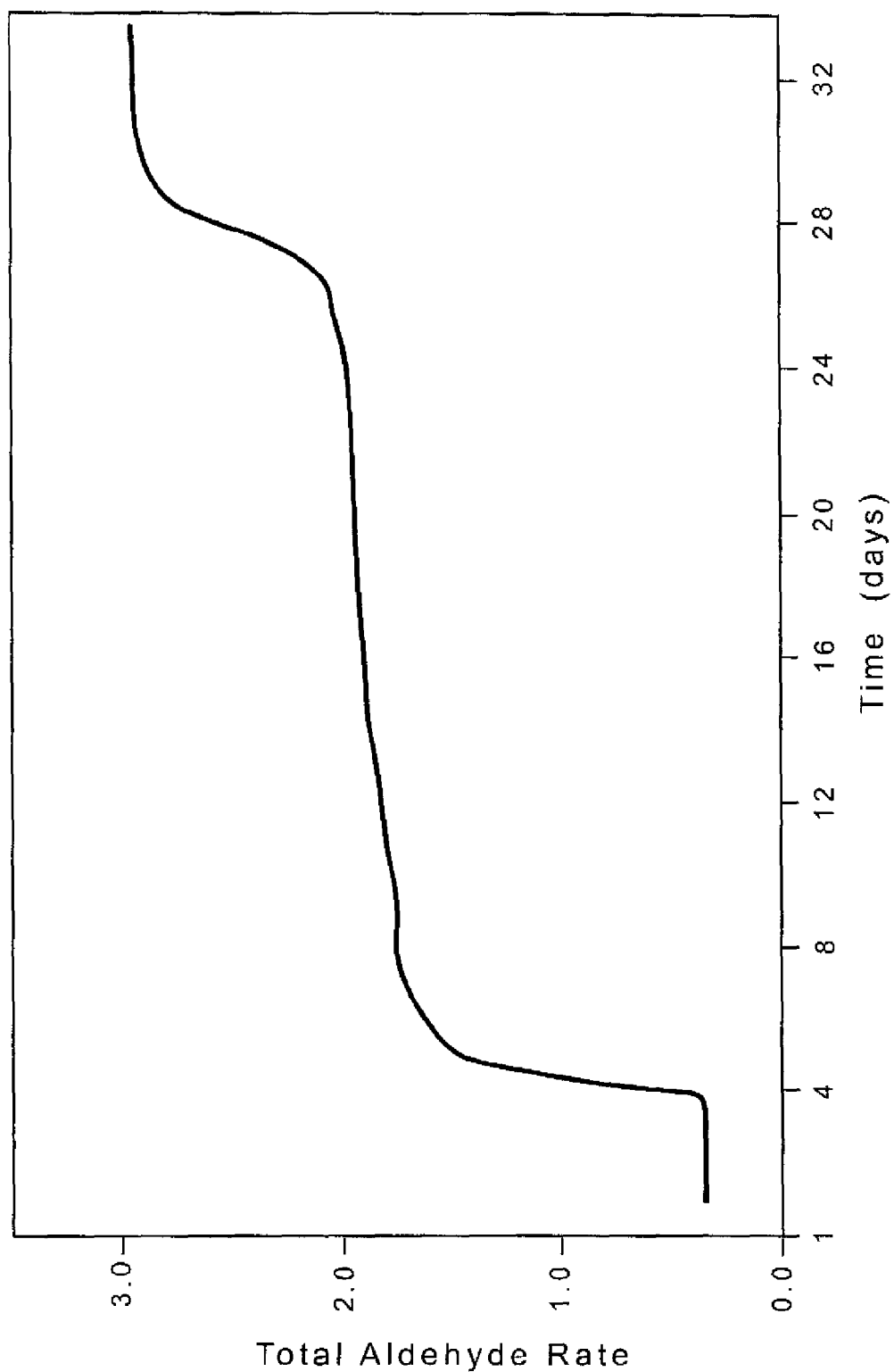
FIG. 4 is a plot of the rate of product formation expressed in $lb/ft^3$ cat-hr. as a function of on-stream time for Example 7.

The catalyst is used to hydroformylate propylene according to the procedure of Example 5, except that the experiment is carried out at 80° C. and 150 psig with $H_2$=1.42 SLH, CO=0.8 SLH, propylene=1.86 SLH and $N_2$=7.0 SLH. The resulting data is shown in FIG. 4.

The $N_2$ is shut off on Day 4, all other conditions remaining the same. On Day 8 the activity=1.5 lb/ft3-cat hr and the n/i=10.3. On Day 28 the temperature is increased to 90° C. The activity increases to 3 lb/ft3-cat hr and the n/i decreases to 5.

Example 8

Includes Buffer Wash

A catalyst is prepared as described in Example 5. In this example the feed is 1-butene. The purpose is to determine whether 1-butene is readily hydroformylated with the vapor phase catalyst.

Figure 5:
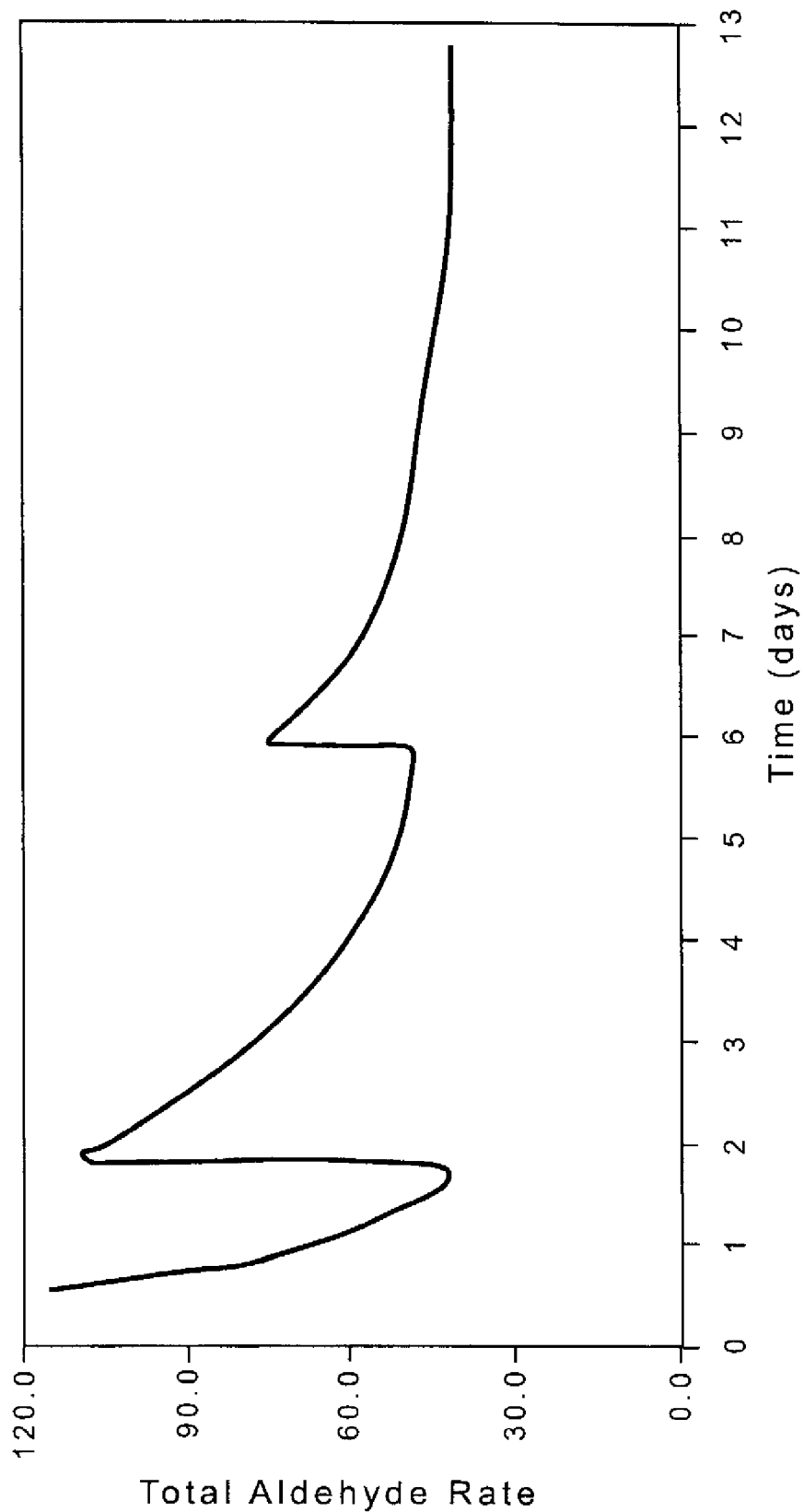
FIG. 5 is a plot of the rate of product formation expressed in $lb/ft^3$ cat-hr. as a function of on-stream time for Example 8.

The catalyst is activated by heating under a $H_2$:CO=1:1 atmosphere at 70° C. for 2 hours. The flow rate is about 10 SLH. After this time, 1-butene is added and the flows are adjusted to 1-butene=6.74 SLH, $H_2$=5.2 SLH, and CO=3.2 SLH. Pressure is set at 50 psig and temperature at 70° C. The catalyst is initially hyperactive producing only n-valeraldehyde and i-valeraldehyde. After eight hours the n-valeraldehyde activity is 82 lb/ft$^3$ cat-hr and the n/i=112. The 1-butene conversion is approximately 55%. These initial results clearly show that hydroformylation of 1-butene occurs with this catalyst. The results are shown in FIG. 5.

After approximately 24 hours of operation n-valeraldehyde activity declines to 47 lb/ft3 cat-hr. At this point the pressure is dropped to 1 atm and syn gas/propylene are shut off and $N_2$ is started. The catalyst bed is covered with 4 ml of sodium phosphate buffer solution. The buffer remains in place for 15 minutes and is then syringed off. The catalyst is reactivated for 2 hours at 80° C., 100 psig with $H_2$ and CO, and then the original flows are reestablished. As shown in FIG. 5, the high n-valeraldehyde activity is regained with a rate of 110 lb/ft3 cat-hr at the start of Day 2. The activity declines to about 47 lb/ft3 cat-hr by Day 5. On Day 6 the 1-butene flow is increased 20%. This causes a spike in the rate followed by a rate decrease. After 12 hours the n-valeraldehyde activity=60 lb/ft3 cat-hr and n/i=142. The butene is increased two times on Day 7, first by 20% and then by 10% and the conditions are then maintained until the run is terminated.

The n-valeraldehyde activity=58 lb/ft3 cat-hr and n/i=208 on Day 9. The activity declines to 46.4 and the run is terminated on Day 13.

What is claimed is:

1. A hydroformylation process for production of at least one aldehyde product, the process comprising: contacting under gas phase reaction conditions carbon monoxide, hydrogen and one or more olefinically-unsaturated compounds in the presence of a hydroformylation catalyst, wherein the catalyst comprises a catalytic metal and a ligand comprising at least one organophosphite ligand, wherein the catalyst is physisorbed on a support, and wherein water vapor is present at least part of the time.

2. The process of claim 1 wherein additional quantities of ligand are contacted with the catalyst at least once after some aldehyde is produced.

3. The process of claim 1 wherein the catalyst is contacted with a buffer solution after some aldehyde is produced.

4. The process of claim 1 wherein the amount of water in moles is at least about 0.001 times the amount of Rh in moles.

5. The process of claim 1 herein the ligand comprises an organopolyphosphite ligand represented by the following formula:

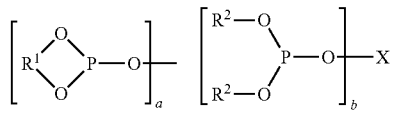

wherein X represents a substituted or unsubstituted n-valent organic bridging radical containing from 2 to 40 carbon atoms, each $R^1$ is the same or different and represents a divalent organic radical containing from 4 to 40 carbon atoms, each $R^2$ is the same or different and represents a substituted or unsubstituted monovalent hydrocarbon radical containing from 1 to 24 carbon atoms, a and b can be the same or different and each have a value of 0 to 6, with the proviso that the sum of a+b is 2 to 6 and n equals a+b.

6. The process of claim 1 wherein the process employs the vent stream of a hydroformylation reactor as a feed stream.

7. The process of claim 1 wherein additional amounts of ligand are provided to the reaction zone at least once following the start of the hydroformylation reaction.

8. The process of claim 1 wherein the transition metal is a Group VIII metal selected from rhodium, cobalt, iridium, ruthenium, and mixtures thereof.

9. The process of claim 1 wherein a mixture of organopolyphosphite ligands is employed; or wherein a mixture of organomonophosphite ligands is employed; or wherein together a mixture of organopolyphosphite ligands and a mixture of organomonophosphite ligands are employed.

10. A hydroformylation process for continuous production of at least one aldehyde product, the process comprising the steps of: contacting under continuous reaction conditions in a hydroformylation reaction gas, one or more $C_{2-4}$ achiral olefins, carbon monoxide, and hydrogen in the presence of a catalytic metal-ligand complex comprising a complex of Ligand A having the formula,

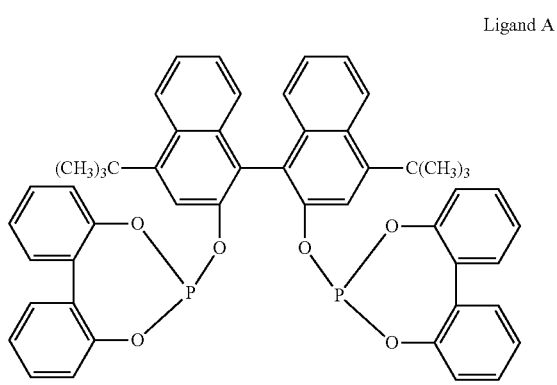 [SMILES: CC(C)(C)c1cc(Op2oc3ccccc3c3ccccc3o2)c(-c2c(Op3oc4ccccc4c4ccccc4o3)cc(C(C)(C)C)c3ccccc23)c2ccccc12]

Ligand A and a catalytic metal, wherein the metal comprises rhodium, and wherein the complex is physisorbed on a support, the contacting being conducted in a manner such that the process temperature is greater than about −25° C. and less than about 200° C., the total gas pressure comprising carbon monoxide, hydrogen, and olefinic reactant(s) is greater than about 25 psia (172 kPa) and less than about 2,000 psia (13,789 kPa), and wherein water vapor is present at least part of the time and the amount of water is at least about 0.001 molar equivalent of water per equivalent of Rh per day.

11. A process for production of at least one aldehyde product via a hydroformylation reaction, the process comprising: (a) contacting in a reaction zone under gas phase reaction conditions, carbon monoxide, hydrogen and one or more olefinically-unsaturated compounds, in the presence of a hydroformylation catalyst, wherein the catalyst is a supported catalyst comprising a catalytic metal and a ligand comprising at least one organophosphite ligand, wherein the catalyst is physisorbed on a support, and wherein water vapor is present at least part of the time in an amount that is sufficient to substantially maintain the activity of the reaction; and at least one of the following steps:

(b) adding additional amounts of ligand to the reaction zone at least once following the start of the hydroformylation reaction; and (c) contacting the supported catalyst with a buffer.

12. The process of claim 11 wherein the buffer is in a liquid solution, the reaction is stopped prior to contacting the catalyst with the buffer, the buffer is substantially removed from the reaction zone after the contacting, and wherein the reaction is restarted.

* * * * *